US006015709A

United States Patent [19]

Natesan

[11] Patent Number: 6,015,709
[45] Date of Patent: Jan. 18, 2000

[54] TRANSCRIPTIONAL ACTIVATORS, AND COMPOSITIONS AND USES RELATED THERETO

[75] Inventor: Sridaran Natesan, Chestnut Hill, Mass.

[73] Assignee: ARIAD Pharmaceuticals, Inc., Cambridge, Mass.

[21] Appl. No.: 08/920,610

[22] Filed: Aug. 27, 1997

Related U.S. Application Data

[63] Continuation-in-part of application No. 08/918,401, Aug. 26, 1997, abandoned.

[51] Int. Cl.$^7$ .............................. C12N 1/15; C12N 1/21; C12N 5/10; C12N 15/62
[52] U.S. Cl. ................. 435/366; 435/252.3; 435/254.11; 435/325; 536/23.4
[58] Field of Search ........................... 435/252.3, 254.11, 435/325, 366; 536/23.1, 23.4; 935/33, 34, 36

[56] References Cited

U.S. PATENT DOCUMENTS

| 5,573,925 | 11/1996 | Halazonetis | 435/69.7 |
| 5,654,168 | 8/1997 | Bujard et al. | 435/69.1 |

FOREIGN PATENT DOCUMENTS

| 0 685 493 A1 | 12/1994 | European Pat. Off. . |
| WO 93/14108 | 7/1993 | WIPO . |
| WO 97/08550 | 3/1997 | WIPO . |
| WO 97/31113 | 8/1997 | WIPO . |
| WO 97/44447 | 11/1997 | WIPO . |

OTHER PUBLICATIONS

Lee, H. et al., "Hormone–dependent Transactivation by Estrogen Receptor Chimeras That Do Not Interact with hsp90", *J. Biol. Chem.*, 271(42): 25727–26730 (1996).
Sauer, F., "Multiple TaF$_{II}$s Directing Synergistic Activation of Transcription", *Science* 270: 1783–1788, (1995).
Pruschy, M., "Mechanistic Studies of a Signaling Pathway Activated by the Organic Dimerizer FK1012", *Chemistry & Biology*, 1(3): 163–171 (1994).
Becker, D. et al., "Fusion of Adenovirus E1A to the Glucocorticoid Receptor by High–Resolution Deletion Cloning Creates Hormonally Inducible Viral Transactivator", *Mol. Cell. Biol.*, 9(9): 3878–3887 (1989).
Paal, K., "Basal Transcription Factors TBP and TFIB and the Viral Coactivator E1A 13S Bind with Distinct Affinities and Kinetics to the Transactivation Domain of NF–kB p65", *Nucleic Acids Research*, 25(5): 1050–1055 (1997).
Luo, Y., Mammalian Two–Hybrid System: A Complementary Approach to the Yeast Two–Hybrid System, *BioTechniques*, 22(2): 350–352 (1997).
Dang, C. et al., "Intracelular Leucine Zipper Interactions Suggest C–MYC Hetero–oligomerization," *Mol. Cell Biol.*, 11 (2): 954–962 (1991).
Kodadek, T., et al., "The Dangers of 'Splicing and Dicing': on the Use of Chimeric Transcriptional Activators in Vitro," *Chemistry and Biology*, 2(4): 187–194 (1995).
Emami, K. H., et al., "A Synergistic Increase in Potency of a Multimerized VP16 Transcriptional Activation Domain," *EMBO J.*, 11(13): 5005–5012 (1992).
Le Douarin, B. et al., "A New Version of the Two–hybrid Assay for Detection of Protein–protein Interactions," *Nucleic Acids Res.*, 23(5): 876–8 (1995).
Remacle J. E., et al., "Three Classes of Mammalian Transcription Activation Domain Stimulate Transcription in *Schizosaccharomyces Pombe*," *EMBO J.* ,16 (18): 5722–5729 (1997).
White, J., et al., "The Acidic Transcriptional Activator GAL–VP16 Acts on Preformed Template–committed Complexes," *EMBO J.*, 11 (6): 2229–2240 (1992).
Sublett, J., et al., "The Alveolar Rhabdomyosarcoma PAX3/ FKHR Fusion Protein is a Transcriptional Activator," *Oncogene*, 11(3): 545–552 (1995).
Chapman, M. et al., "Transcriptional Control of Steroid– –Regulated Apoptosis in Murine Tymoma Cells," *Mol. Endocrinol.*, 10: 967–978 (1996).
Tate, B. et al., "A Systematic Analysis of the AF–2 Domain of Human Retinoic Acid Receptor α Reveals Amino Acids Critical for Transcriptional Activation and Conformational Integrity", *FASEB J.*, 10: 1524–1531 (1996).
Orphanides, G. et al., "The General Transcription Factors of RNA Polymerase II", *Genes & Dev.*, 10: 2657–2683 (1996).
Zeng, X. and Hu, J., "Detection of Tetramerization Domains in Vivo by Cooperative DNA Binding to Tandem λ Operator Sites", *Gene*, 185: 245–149 (1997).
Lin, Y.–S. et al., "GAL4 Derivatives Function Alone and Synergistically with Mammalian Activators in Vitro", *Cell*, 54: 659–664 (1988).
Hollenberg, M. and Evans, R., "Multiple Cooperative Trans– –Activation Domains of the Human Glucocorticoid Receptor", *Cell*, 55: 889–906 (1988).
Schmitz, M. et al., "Transactivation Domain 2 (TA$_2$) of p65 NF–κB", *J. Biol. Chem.*, 270: 15576–15584 (1995).
Gerber et al. (1994) Transcriptional activation modulated by homopolymeric glutamine and proline stretches. Science 263:808–811, Feb. 1994.
Wang et al. (1997) Positive and negative regulation of gene expression in eukaryotic cells with an inducible transcriptional regulator. Gene Therapy 4:432–441, May 1997.
Verma et al. (1997) Gene therapy–promises, problems and prospects. Nature 389:239–242, Sep. 1997.

*Primary Examiner*—Nancy Degen
*Assistant Examiner*—Robert Schwartzman
*Attorney, Agent, or Firm*—David L. Berstein; Sharon F. Hausdorff; Matthew P. Vincent

[57] ABSTRACT

The present invention relates to chimeric transcriptional activators.

44 Claims, 10 Drawing Sheets

6,015,709

TRANSCRIPTIONAL ACTIVATORS, AND COMPOSITIONS AND USES RELATED THERETO

This application is a continuation-in-part of U.S. application Ser. No. 08/918,401 entitled "Transcriptional Activators, and Compositions and Uses Thereto", filed Aug. 26, 1997, now abandoned.

BACKGROUND OF THE INVENTION

A large number of biological and clinical protocols, among others, gene therapy, production of biological materials, and biological research, depend on the ability to elicit specific and high-level expression of genes encoding RNAs or proteins of therapeutic, commercial, or experimental value. A variety of expression systems have been developed, including regulated expression systems, involving allosteric on switches triggered by tetracycline, RU486 and ecdysone, as well as dimerization based on-off switches triggered by FK1012, FK-CsA, rapamycin and analogs thereof. See e.g. Clackson, "Controlling mammalian gene expression with small molecules" Current Opinion in Chemical Biology 1997, 1:210–218. Still, achieving a sufficiently high level of expression for clinical or other utility in genetically engineered cells in various contexts, including within whole organisms, has often been a limiting problem. Various approaches for addressing this problem, including the search for stronger transcriptional promoters or higher transfection efficiencies, have in many cases not met with success. Meanwhile, in various lines of research with transcription factors, promising results in transient transfection models have not been borne out with chromosomally integrated reporter gene constructs. Furthermore, overexpression of transcription factors is commonly associated with toxicity to the host cell. Despite those precedents, this invention takes a novel approach to the challenge of optimizing gene expression through new uses of, and new designs for, transcription factor proteins which are expressed within the engineered cells containing the target gene. The invention provides improved methods and materials for achieving high-level expression of a target gene in genetically engineered cells, including genetically engineered cells within whole organisms.

SUMMARY OF THE INVENTION

In the course of our research on transcription activation, we have quite unexpectedly discovered an important phenomenon which may explain the absence of greater progress in the discovery and/or optimization of more powerful transcription activating domains. Briefly, we have made the unexpected discovery that in conventional transient transfection experiments of the sort typically used in this field to study transcription activation, as the number or apparent potency of activation domains increases, the observed level of transcription increases to a maximum and then levels off or decreases in a phenomenon termed "squelching". However, when analogous experiments are conducted using stably incorporated reporter genes in place of transiently transfected reporter genes, squelching is avoided, and instead, an unimpeded structure-activity relationship can be observed for various transcription activation domains and modifications thereof. With the blinders otherwise imposed by squelching now removed, we have made significant advances in the design and implementation of transcription activation domains in chimeric proteins and transcription systems.

This invention encompasses nucleic acid constructs encoding various chimeric transcription activator proteins (also referred to below as "composite activators") and in some embodiments auxiliary chimeric proteins, as well as related materials and methods, as disclosed in greater detail below. A number of illustrative embodiments are highlighted below.

For example, a number of embodiments of the invention involve a nucleic acid encoding a chimeric transcription activator protein which activates the transcription of a gene to which the chimeric transcription activator protein is targeted. Targeting may be effected via one or more DNA-binding domains ("DBDs") which bind to a DNA sequence to which a target gene is operatively linked. The DBD(s) may be present within the chimeric transcription activator protein or may be provided by an auxiliary chimeric protein as disclosed in extensive detail below.

In certain embodiments of the invention the chimeric transcription activator protein contains at least one composite transcription activation domain ("TAD") and at least one DBD. The composite TAD comprises a continuous polypeptide region containing two or more component polypeptide regions (also referred to below as "activation tags"), at least two of which do not occur together in the same gene product in nature. In certain of these embodiments the chimeric protein comprises a ligand binding domain for allosteric activation, e.g. a receptor domain capable of binding a cell permeant ligand such as tetracycline or an analog thereof or a steroid such as RU486 or ecdysone, for example. In such cases, the chimeric transcription activator selectively activates transcription of a target gene in the presence of the respective ligand. In other embodiments the chimeric transcription activator is capable of activating target gene expression constitutively, i.e., without the need for the presence of any such ligand.

In other embodiments, the chimeric transcription activator protein contains at least one composite TAD comprising three or more component polypeptide regions, at least two of which do not occur together in the same gene product in nature, and at least one additional domain which is heterologous with respect to at least one of the component polypeptide regions of the composite TAD. The additional domain(s) may include a DBD or a receptor domain for an oligomerizing ligand. Oligomerizing ligands are multivalent, preferably cell permeant, compounds, generally having a molecular weight below about 5 kD, and preferably below about 2 kD, which mediate the formation of complexes with proteins containing receptor domains to which the ligands binds. Non-limiting, illustrative examples of oligomerizing ligands include FK1012 (with respect to proteins containing FKBP domains), coumermycin (with respect to proteins containing DNA Gyrase domains), fujisporin (with respect to proteins containing cyclophilin and FKBP domains, respectively) and rapamycin (with respect to proteins containing FKBP and FRAP domains, respectively).

In still other embodiments, the chimeric transcription activator protein contains at least one composite TAD comprising a continuous polypeptide region containing two or more component polypeptide regions, at least two of which do not occur together in the same gene product in nature, or at least not in the same order, arrangement or number as found in the chimeric protein of this invention, and at least one additional domain which is heterologous with respect to at least one of the component polypeptide regions of the composite TAD. In some of these embodiments, the components are all of human origin. In other of these embodiments, at least one of the heterologous domains comprises a domain derived from an immunophilin, cyclophilin, calcineurin, FRAP or DNA gyrase domain; a domain derived from a receptor for tetracycline or ecdysone or another steroid; or a composite DNA binding domain.

In still other embodiments, the chimeric transcription activator protein contains at least one transcription activation domain, which may be a previously known transcription activation domain such as VPI6, a novel truncated p65-derived activation domain disclosed in detail below or a composite TAD as described herein, and at least one bundling domain. A bundling domain is a domain permitting assembly of complexes of two or more proteins each of which comprises a copy of the bundling domain or a close variant thereof. Non-limiting examples of bundling domains include domains derived from p53 or the E coli lac repressor as well as various leucine zipper domains. Bundling domains are distinguished from heterooligomerizing proteins such as the FKBP/calcineurin pair, the FKBP/FRAP pair, the cyclophilin/calcineurin pair, the RXR/TBP pair, for example, which form heterooligomers of proteins containing very different binding domains. In contrast, bundling domains permit oligomerization between proteins containing the same bundling domains or very similar variants thereof, and do so without the need for ligand-mediation.

In various embodiments, one or more of the DBD, receptor domain, oligomerizing ligand binding domain or other additional heterologous domain is heterologous with respect to at least one of the component polypeptide regions of the composite transcription activation domain. In other embodiments, one or more of such additional heterologous domains is heterologous with respect to at least two of the component polypeptide regions of the composite transcription activation domain. In one embodiment, the composite activator protein includes at least two different activation tags from heterologous sources, e.g., activation tags which are derived from two or more different transcription factors or co-activators and which do not naturally occur together in the same protein. While not wishing to be bound by any particular mechanistic hypothesis, two or more of the activation tags of a composite activator, more preferably two which are derived from disparate proteins, may recruit TAFs which are not required for basal activation of a gene. Through the activation tags, the chimeric activator may recapitulate the interaction of several otherwise discrete factors with the polymerase complex, or provide novel contacts with that complex, which interactions may recruit and/or stabilize the formation of activator-dependent transcriptional complexes.

In this context, it has also been discovered that a variety of activation tags can be repeated multiple times in the same chimeric protein, or multiply associated therewith, with a concomitant increase in transcriptional activation. The repetitive activation tag embodiment can be combined with other activation tags, e.g., from the same or heterologous sources as the repeated activation tag(s).

Another aspect of the invention relates to the identification of novel activation tags. In this regard, an activation tag has been identified in the NF-kB transcription factor subunit p65. The so-called "alanine/proline rich" or "AP" activation tag of p65 extends from about amino acids 361 to about amino acid 450 of that protein. See SEQ ID No. 2. Similar AP activation tags are also present in, e.g., the p53 and CTF proteins. The present invention also contemplates fragments of p65 (or homologous sequences thereto, e.g., from p53 or CTF) which are about 75, 60, 50, 30 or even 20 amino acid residues in length. In other embodiments, the AP activation tag has an amino acid sequence at least 95%, 90%, 80% or 70% identical to the AP activation tag of SEQ ID No. 2.

The subject chimeric activators can be used to drive high levels of transcription from naturally-occurring, or otherwise genomically-integrated genes. The chimeric activators of the invention are particularly useful for activating transcription of integrated single copy genes, which in the past have not successfully transactivated at appreciable levels. In preferred embodiments the level of expression of a chromosomally-integrated target gene achieved with the novel and/or composite transcription activation domains disclosed herein is at least two-fold, preferably three-fold, more preferably five-fold, and optimally ten-fold or better greater than expression levels achieved using the VP 16 domain as the transcription activation domain in the analgous expression system, as measured in a scientifically valid comparison.

This invention also encompasses nucleic acid compositions comprising a first nucleic acid encoding a chimeric transcription activator protein which contains one or more ligand-binding domains for an oligomerizing ligand such as described above and a second nucleic acid encoding a chimeric DNA-binding protein which comprises at least one DNA-binding domain and at least one ligand binding domain for a cell permeant ligand. Thus, the chimeric proteins encoded by these nucleic acids each contain one or more ligand-binding domains for binding to an oligomerizing ligand which mediates the dimerization or higher-order hetero-oligomerization of the chimeric proteins. In some embodiments, one or both of the chimeric proteins contains two or more ligand-biding domains. The nucleic acid composition may further comprise a target gene construct comprising a target gene operatively linked to a transcriptional regulatory element which includes a DNA sequence to which the chimeric DNA-binding protein binds.

This invention also encompasses nucleic acid compositions comprising a first nucleic acid encoding a chimeric transcription activator protein which contains one or more composite TADs and one or more DBDs, such as described above, and a second nucleic acid comprising a target gene construct comprising a target gene operatively linked to a transcriptional regulatory element which includes a DNA sequence to which the chimeric transcription activator protein binds.

A nucleic acid encoding a chimeric protein of this invention may be operably linked to a transcriptional regulatory element permitting expression of the chimeric protein in cells. The various nucleic acids may be provided in DNA vectors as disclosed below.

The invention also encompasses methods for engineering cells for the regulated or constitutive expression of a heterologous target gene. That method involves introducing nucleic acids or nucleic acid compositions of this invention into the cells using methods and materials permitting uptake by the cells of the nucleic acids. In embodiments of particular interest, the target gene is integrated within the chromosomes of the host cells. In some cases the transfected cells are selected and separately recovered from non-transfected cells. In certain embodiments the cells are grown in culture. In some embodiments the cells are engineered in vivo (within a whole organism), while in other embodiments cells are transfected in vitro and the transfected cells and/or their progeny are subsequently introduced into whole organisms. In the latter case, the engineered cells may be encapsulated prior to introduction into the organism.

Engineered cells which contain one or more nucleic acids or nucleic acid compositions of this invention are also encompassed. Again, engineered cells in which the target gene is stably integrated within the cell's chromosomes are of particular interest.

This invention further encompasses methods for effecting expression of a target gene which comprises maintaining genetically engineered host cells as described herein under conditions suitable for gene expression. In regulated expression embodiments, this will involve contacting the cells, in vitro or in vivo, with the ligand or oligomerizing agent which binds to one or both of the chimeric proteins.

Applications of this invention include transcription of genes, constitutively or in a drug-dependent manner in vitro, e.g. for the production of a desired protein which may be separately recovered, for achieving higher levels of expression in transcription based assays (including two-hybrid assays), and for the regulated expression of required viral genes in producer cells lines used for production of recombinant viruses (e.g. for the regulated expression of AAV rep and/or cap genes in host cells used for the production of recombinant AAV). Other applications include in vivo applications such as the constitutive or regulated expression of a target gene of interest in an animal model (e.g. for research or veterinary purposes) as well as for the constitutive or regulated expression of a target gene of interest in a human subject, e.g. in the case of gene therapy. In the case of human gene therapy, it will often be preferred that the components of the chimeric proteins be of human origin and/or that the engineered cells be encapsulated.

Other features and advantages of the invention will be apparent from the following detailed description and claims.

DETAILED DESCRIPTION OF THE INVENTION

I. General

Figure 1A:
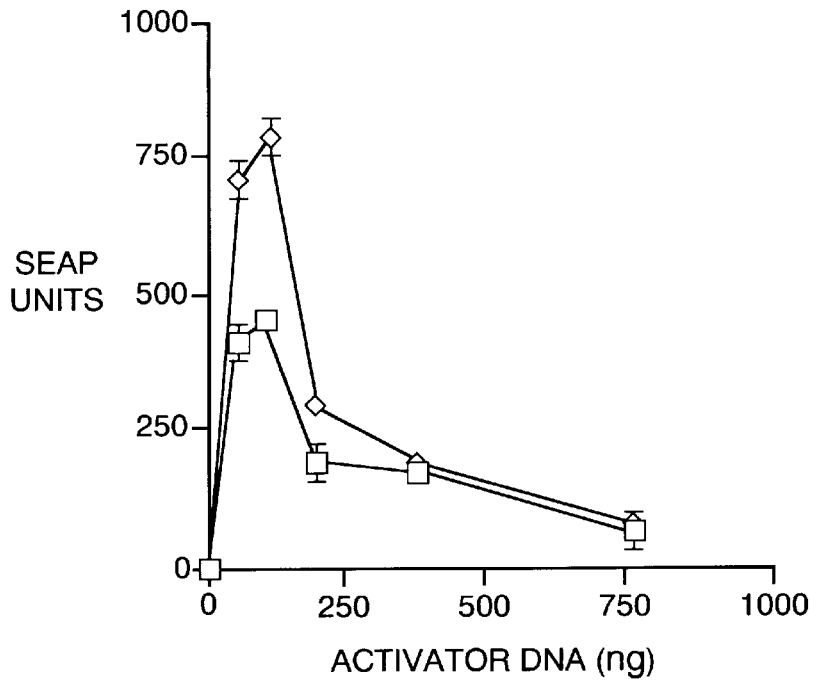
FIG. 1A shows the level of reporter gene expression (in EAP Units) from the plasmid 5xGAL4-IL2-SEAP transiently transfected into HT1080 cells cotransfected with various amounts of GAL4-p65 (diamonds) or GAL4-VP16 (squares) expression constructs (Activator DNA). Mean values of SEAP activity secreted into the medium are shown (+/–S.D.).

Protein-encoding genes in eukaryotes are transcribed by RNA polymerase II (pol II), a multisubunit enzyme that is brought to an appropriate gene promoter (pol II promoter) through the assembly of a pre-initiation complex comprising a number of general transcription factors. The multisubunit protein complex TFIID is required for transcription by most, if not all, promoters targeted by pol II. Whereas the TATA-box binding protein (TBP) of TFIID is sufficient for basal transcription, pol II transcription is also regulated by gene-specific activator proteins. Activator-dependent transcription requires, inter alia, TBP-associated proteins (TAFs) and other transcriptional cofactors. One of the important concepts to emerge from studies of eukaryotic gene expression is that activators of pol II-dependent transcription are composed of functional modules whose abilities to bind to subunits of the ultimate pol II complexes regulates transcriptional activity of a nearby gene.

The present invention pertains to nucleic acid molecules and proteins which can be used to regulate the expression of genes in eukaryotic cells.

One aspect of the present invention relates to chimeric transcriptional activators ("composite activators") which are derived to include a multiplicity of heterologous "activation tags" (further defined infra), e.g., polypeptide sequences capable of affecting transcriptional activation, as for example, affecting the assembly or stability of an active polymerase complex. It has been discovered that activation tags from disparate proteins can be combined in a single polypeptide, or artificially recruited by a complex to a single recognition element and retain the ability to synergistically activate transcription. In its simplest elaboration, the chimeric activator includes at least two different activation tags from heterologous sources, e.g., activation tags which are derived from two or more different transcription factors or co-activators and which do not naturally occur together in the same protein. As described further in the appended examples, constructs of this type are observed to form potent transcriptional activators with a variety of uses. Accordingly, the invention provides composite transcriptional activators which are derived with activation tags from at least two separate proteins.

In this context, it has also been discovered that a variety of activation tags can be repeated multiple times in the chimeric protein, or multiply associated therewith, with a concomitant increase in transcriptional activation. This result was unexpected in light of, as an example, the belief that squelching observed in the systems of the prior art was a result of a rate limiting step involving the availability of general transcription factors, e.g., those of the TFIID complex. Accordingly, another type of composite activator of the present invention is one wherein multiple copies of an activation tag are repeated, e.g., from 2 to 20 times, in a given composite activator. The repetitive activation tag embodiment can be combined with other activation tags, e.g., from the same or heterologous sources as the repeated activation tag(s). As described with greater detail herein, in either of the above embodiments, the activation tag can itself induce activator dependent transcription. Alternatively, the activation tag may be one which alone is insufficient to induce activator-dependent transcription, but rather produces a synergistic effect when provided with a second activation tag which itself has some ability to induce activator-dependent transcription. The composite activators of the present invention may be generated to include DNA binding domains, ligand binding domains (LBDs) and/or oligomerization domains (ODs).

Another aspect of the invention relates to the identification of novel activation tags. In this regard, an activation tag has been identified in the NF-kB transcription factor subunit p65. The so-called "alanine/proline rich" or "AP" activation tag of p65 extends from about amino acids 361 to about amino acid 450 of that protein. See SEQ ID No. 2. Similar AP activation tags are also present in, e.g., the p53 and CTF proteins. As described in the Examples, the presence of one or several copies of the AP domain alone in a protein does not provide the ability to induce activator-dependent transcriptional activation. However, when linked to activation tags which are themselves capable of inducing some level of activator-dependent transcription, e.g., another portion of p65 or VP16, the AP activation tag synergizes with the second activation domain to induce an increase in the level of activated transcription. The AP activation tag can be used, for example, to construct chimeric transcription factors, to generate drug screening assays, or as a competitive inhibitor of p65 or other transcription factors which utilize the AP activation tag to form transcriptional complexes.

Still another aspect of the present invention relates to the observation that, in contrast to episomal genes, the level of transcription of an integrated gene is directly related to the number of activation tags that can be delivered to the gene.

While not wishing to be bound by any particular mechanistic theory, the inhibition of transcription of an episomal gene in the presence of multiple activation unit might result from the sequestration by the activator (unbound to DNA) of either (i) an adaptor component necessary to bridge the activator with the basal machinery, and/or (ii) a basal component. In contrast, transcription of an integrated gene appears to be enhanced by delivery of additional activation units to the promoter sequence(s) of the gene. Thus, the subject chimeric activators can be used to drive high levels of transcription from naturally-occuring, or otherwise genomically-integrated genes. The chimeric activators of the invention are particularly useful for activating transcription of integrated single copy genes, which in the past have not successfully transactivated at appreciable levels.

II. Definitions

For convenience, the meaning of certain terms and phrases employed in the specification, examples, and appended claims are provided below.

As used herein, the term "gene" or "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides.

The term "operably linked" when referring to a transcriptional regulatory sequence and a coding sequence is intended to mean that the regulatory sequence is associated with the coding sequence in such a manner as to facilitate transcription of the coding sequence in an activator-dependent fashion.

The terms "protein", "polypeptide" and "peptide" are used interchangeably herein when referring to a gene product, e.g., as may be encoded by a coding sequence. "Transcriptional regulatory sequence", also termed herein "regulatory element", "regulatory sequence" or "regulatory element", are generic terms used throughout the specification to refer to DNA sequences, such as initiation signals, enhancers, and promoters, which induce or control transcription of protein coding sequences with which they are operably linked. The term "enhancer", also referred to herein as "enhancer element", is intended to include regulatory elements capable of increasing, stimulating, or enhancing transcription from a basic promoter. The term "silencer", also referred to herein as "silencer element" is intended to include regulatory elements capable of decreasing, inhibiting, or repressing transcription from a basic promoter. Regulatory elements can also be present in genes other than in 5' flanking sequences. Thus, it is possible that regulatory elements of a gene are located in introns, exons, coding regions, and 3' flanking sequences.

The terms "basic promoter" or "minimal promoter", as used herein, are intended to refer to the minimal transcriptional regulatory sequence that is capable of initiating transcription of a selected DNA sequence to which it is operably linked. This term is intended to represent a promoter element providing basal transcription. A basic promoter frequently consists of a TATA box or TATA-like box and is bound by an RNA polymerase and by numerous transcription factors, such as GTFs and TATA box Binding Proteins (TBPs).

The terms "basic promoter" and "regulatory element" further encompass "tissue specific" promoters and regulatory elements, i.e., promoters and regulatory elements which effect expression of the selected DNA sequence preferentially in specific cells (e.g., cells of a specific tissue). Gene expression occurs preferentially in a specific cell if expression in this cell type is significantly higher than expression in other cell types. The terms "promoter" and "regulatory element" also encompass so-called "leaky" promoters and "regulatory elements", which regulate expression of a selected DNA primarily in one tissue, but cause expression in other tissues as well. The terms "promoter" and "regulatory element" also encompass non-tissue specific promoters and regulatory elements, i.e., promoters and regulatory elements which are active in most cell types. Furthermore, a promoter or regulatory element can be a constitutive promoter or regulatory element, i.e., a promoter or regulatory element which constitutively regulates transcription, as opposed to a promoter or regulatory element which is inducible, i.e., a promoter or regulatory element which is active primarily in response to a stimulus. A stimulus can be, e.g., a molecule, such as a hormone, a cytokine, a heavy metal, phorbol esters, cyclic AMP (cAMP), or retinoic acid.

The term "core promoter element" is intended to include the TATA box and the initiator element. "DNA recognition sequence" or "DNA recognition element", as those phrases are used herein, mean a DNA sequence which is capable of binding to one or more DNA-binding domains, e.g., of a transcription factor.

The term "initiator" refers to a short, weakly conserved element that encompasses the transcription start site and which is important for directing the synthesis of properly initiated transcripts. While not wishing to be bound by any one theory, it is thought that TFIID contacts the initiator.

The term "transcription factor" refers to any protein or modified form thereof that is involved in the initiation of transcription but which is not itself a part of the polymerase. Transcription factors are proteins or modified forms thereof, which interact preferentially with specific nucleic acid sequences, i.e., regulatory elements, and which in appropriate conditions stimulate transcription ("transcriptional activators") or repress transcription ("transcriptional repressors"). Some transcription factors are active when they are in the form of a monomer. Alternatively, other transcription factors are active in the form of oligomers consisting of two or more identical proteins or different proteins (heterodimer). The factors have different actions during the transcription initiation: they may interact with other factors, with the RNA polymerase, with the entire complex, with activators, or with DNA. The factors are generally classifiable into two groups: (i) the general transcription factors, and (ii) the transcription activators. Transcription factors usually contain one or more regulatory domains.

The term "regulatory domain" refers to any domain which regulates transcription, and includes both activation and repression domains. The term "activation domain" denotes a domain in a transcription factor which positively regulates (increases) the rate of gene transcription. The term "repression domain" denotes a domain in a transcription factor which negatively regulates (inhibits or decreases) the rate of gene transcription.

The term "general transcription factor" used interchangeably herein with the term "GTF" and with "basic transcription factor" refers to proteins or protein complexes which work in concert with RNA Polymerase II to bring about promoter recognition and accurate transcription initiation.

These proteins constitute, together with the RNA polymerase II the Transcription Initiation Complex. GTFs include TFIIA, TFIIB, TFIID, TFIIE, TFIIF, and TFIIH. These GTFs are usually sufficient to direct basal levels of transcription in vitro from strong promoters (i.e., those containing TATA boxes). Several GTF interact with one another and/or with RNA Polymerase II. For example, TFIIE interacts with TFIIH and RNA Polymerase II, TFII F interacts with RNA Polymerase II and with TFIIB, and TFII B interacts with TBP from TFIID and RNA Polymerase II.

The term "transcriptional activator" as used herein refers to a protein or protein complex which is capable of enhancing the efficiency with which the basal transcription complex performs, i.e., activating transcription. Thus, as used herein, a transcriptional activator can be a single protein or alternatively it can be composed of several units at least some of which are not covalently linked to each other. A transcriptional activator typically has a modular structure, i.e., comprises various domains, such as a DNA binding domain, and one or more transcriptional activation tags. Some transcriptional activators may engage a subset of GTFs. For example, some transcriptional activators may include activation tags which collectively contact both TFIID and TFIIB. Other transcriptional activators may contact a single GTF.

The term "cofactor" which is used interchangeably herein with the terms "co-activator", "adaptor" and "mediator" refers to proteins which either enhance or repress transcription in a non-gene specific manner, e.g., which lack intrinsic DNA binding specificity. Thus, cofactors are general effectors. Positively acting cofactors do not stimulate basal transcription, but enhance the response to an activator. Positively acting cofactors include PC1, PC2, PC3, PC4, and ACF. TAFs which interact directly with transcriptional activators are also referred to as cofactors.

The term "transcriptional activation tag", also referred to herein as "activation tag", "transcriptional activation unit" and "activation unit", refers to a peptide sequence which is capable of inducing or otherwise potentiating activator-dependent transcription, either on its own or when linked covalently or non-covalently to another transcriptional activation unit. As opposed to a transcriptional activator generally, an activation tag corresponds to a minimal polypeptide sequence which retains the ability to interact directly or indirectly with a transcription factor. Of course, unless otherwise clear from the context, where a chimeric protein is referred to as "including" or "comprising" an activation tag, it will be understood that other portions of the protein from which the tag is derived can be included. Transcriptional activation tags can be rich in certain amino acids. For example, a transcriptional activation unit can be a peptide rich in acidic residues, glutamine, proline, or serine and threonine residues. Yet other transcriptional activators can be rich in isoleucine or basic amino acid residues (see, e.g., Triezenberg (1995) Cur. Opin. Gen. Develop. 5:190, and references therein). For instance, an activation tag can be a peptide motif of at least about 6 amino acid residues associated with a transcription activation domain, including the well-known "acidic", "glutamine-rich" and "proline-rich" motifs such as the K13 motif from p65, the OCT2 Q domain and the OCT2 P domain, respectively.

A "dimerization domain" is defined as a domain that induces formation of dimers between two proteins having that domain, while a "tetramerization domain" is defined as a domain that induces formation of tetramers amongst proteins containing the tetramerization domain. An "oligomerization domain", generic for both dimerization and tetramerization domains, facilitates formation of oligomers, which can be of any subunit stoiechiometry (of course greater than one).

The term "interact" as used herein is meant to include detectable interactions between molecules, such as can be detected using, for example, a yeast two hybrid assay or by immunoprecipitation. The term interact is also meant to include "binding" interactions between molecules. Interactions may be, for example, protein-protein, protein-nucleic acid, protein-small molecule or small molecule-nucleic acid in nature.

The term "holoenzyme complex" refers to RNA Polymerase II-containing complexes.

The term "squelching" which is used interchangeably herein with the term "activator interference" refers to the inhibition of transcription observed when an activator is present at artificially high concentrations (Ptashne and Gann (1990) Nature 346:329). While not bound by any particular theory, this inhibition is understood to result from the sequestration by the activator (unbound to DNA) of either (i) an adaptor component necessary to bridge the activator with the basal machinery, and/or (ii) a basal component.

The term "subunit", when referring to the subunit of a transcriptional activator, refers to any unit of the transcriptional activator, e.g., a transcriptional activation unit, a DNA binding domain, or a ligand binding domain.

The term "unit", when referring to a unit of a transcription factor, refers generally to a minimum portion of a transcription factor having a specific activity, e.g., transcriptional activation, transcriptional repression, DNA binding, or ligand binding.

As used herein, the term "transfection" means the introduction of a nucleic acid, e.g., an expression vector, into a recipient cell by nucleic acid-mediated gene transfer. The term "transduction" is generally used herein when the transfection with a nucleic acid is by viral delivery of the nucleic acid. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the recombinant protein is disrupted.

As used herein, the term "transgene" refers to a nucleic acid sequence which has been introduced into a cell. Daughter cells deriving from a cell in which a transgene has been introduced are also said to contain the transgene (unless it has been deleted). A transgene can encode, e.g., a polypeptide, partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene). Alternatively, a transgene can also be present in an episome. A transgene can include one or more transcriptional regulatory sequences and any other nucleic acid, (e.g. intron), that may be necessary for optimal expression of a selected coding sequence.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto. "Derived from" as that phrase is used herein indicates a peptide or nucleotide sequence selected from within a given sequence. A peptide or nucleotide sequence derived from a named sequence may contain a small number of modifications relative to the parent sequence, in most cases representing deletion, replacement or insertion of less than about 15%, preferably less than about 10%, and in many cases less than about 5%, of amino acid residues or base pairs present in the parent sequence. In the case of DNAs, one DNA molecule is also considered to be derived from another if the two are capable of selectively hybridizing to one another.

The terms "chimeric", "fusion" and "composite" are used to denote a protein, peptide domain or nucleotide sequence or molecule containing at least two component portions which are mutually heterologous in the sense that they are not, otherwise, found directly (covalently) linked in nature. More specifically, the component portions are not found in the same continuous polypeptide or gene in nature, at least not in the same order or orientation or with the same spacing present in the chimeric protein or composite domain. Such materials contain components derived from at least two different proteins or genes or from at least two non-adjacent portions of the same protein or gene. Composite proteins, and DNA sequences which encode them, are recombinant in the sense that they contain at least two constituent portions which are not otherwise found directly linked (covalently) together in nature.

III. Exemplary Chimeric Activators

In one aspect, the invention provides composite activators comprised of a multiplicity of activation tags fused to, e.g., a DNA-binding domain, a ligand binding domain and/or an oligomerization domain.

A composite transcription activation region consists of a continuous polypeptide region containing two or more reiterated or otherwise heterologous activation tags. The activation tags comprise polypeptide sequences derived from at least two different proteins, polypeptide sequences which do not ordinarily occur in the same orientation relative to one another (including reiterated copies of a polypeptide sequence), or polypeptide sequences which do not occur in nature.

In one embodiment, at least one of the activation tags recruits TFIIA to a TFIID complex to form a "DA" complex, and/or stabilized the formation of a DA complex. Other activation tags recruit, or stabilize, complexes including other TAFs and co-activators required for activator-dependent transcription. For instance, in certain cases the composite activator sequence may recruit TFIIA and TFIIB, TFIIE, TFIIF, or TFIIH. In a preferred embodiment, the composite activator includes at least two different activation tags from the group of acidic activation tags, proline-rich transcription activation tags, serine/threonine-rich activation tags, glutamine-rich activation tags, and AP activation tags, and even more preferably, at least two of those activation tags are selected from disparate proteins (i.e., that do not naturally occur together in the same protein).

Where multiple copies of a particular activation tag are included in the same contiguous polypeptide, the composite activator preferably includes at least 3 copies of the activation tag, but more preferably at least 5, 10, 15, or even at least 20 copies of the tag.

Figure 11:
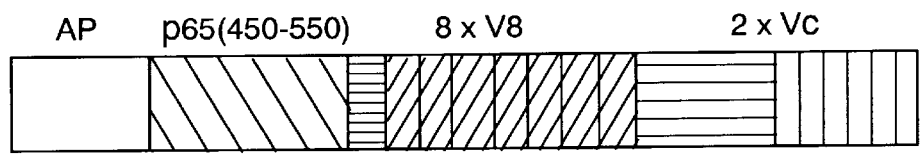
FIG. 11 is a schematic representation of a composite activator.

Shown in FIG. 11 is a representative example of the subject composite activators. In the exemplary composite activator, two or more of the activation tags are from different proteins. The AP activation sequence and the p65 (450–550) activation sequence are derived from the human NF-(B p65 subunit, whereas the V8 domain is an acidic activation tag from the N-terminus of VP16, and the Vc activation tag is a C-terminal portion of VP16. Each of the p65(450–550), V8, and Vc sequences are capable of inducing activator-dependent transcription. Presented in the same polypeptide sequence, these activation tags induce expression of a responsive gene in a synergistic fashion. On the other hand, the AP activation tag on its own is insufficient to induce activator-dependent transcription, but when combined with an activation tag such as the V8 activation tag, the presence of the AP activation tag increases transactivation of the gene relative to the V8 activation tag alone.

Another feature of the illustrated composite activator is the repetition of certain of the activation tag sequences. Reiterating the V8 and Vc activation tags, for example, increases the fortitude of the resulting protein as a transcriptional activator, particularly of genomically integrated genes.

As described in more detail below, the ideal number of activation tags to include, and the relative orientations of the various tags to one another in the composite activators, can be readily determined by techniques known in the art, including high throughput screening using reporter gene-based assays.

Figure 3A:
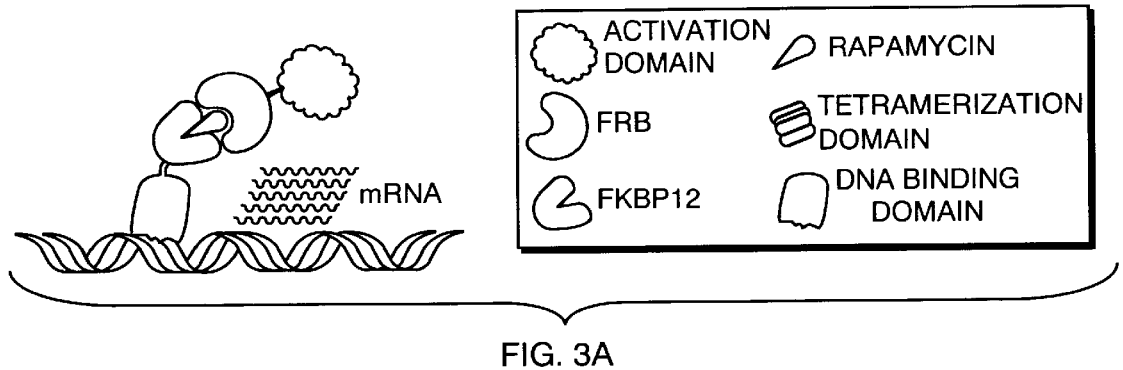
FIG. 3A is a diagrammatic representation of rapamycin-induced dimerization of two fusion proteins, one containing the GAL4 DNA binding domain fused to FKBP12, and the other containing the p65, activation domain fused to FRB, thereby leading to stimulation of target gene expression.
Figure 3B:
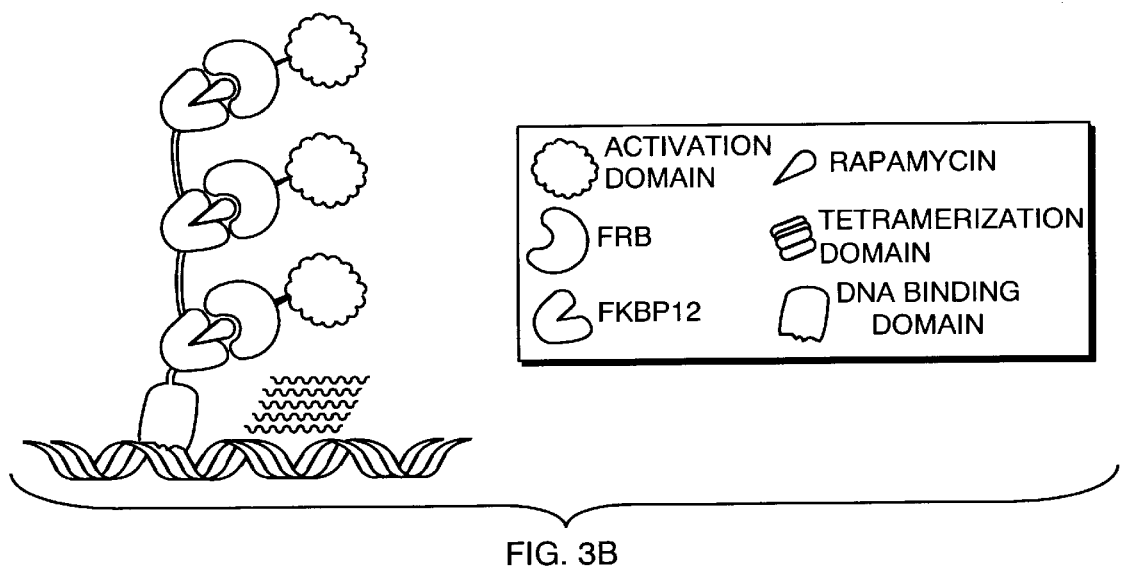
FIG. 3B is a diagrammatic representation of rapamycin-induced dimerization of two fusion proteins, one containing a GAL4 DNA binding domain fused to the three copies of FKB12, and the other containing the p65, activation domain fused to FRB, thereby leading to association of three p65 activation domains with each GAL4 mononer in the presence of rapamycin.
Figure 3C:
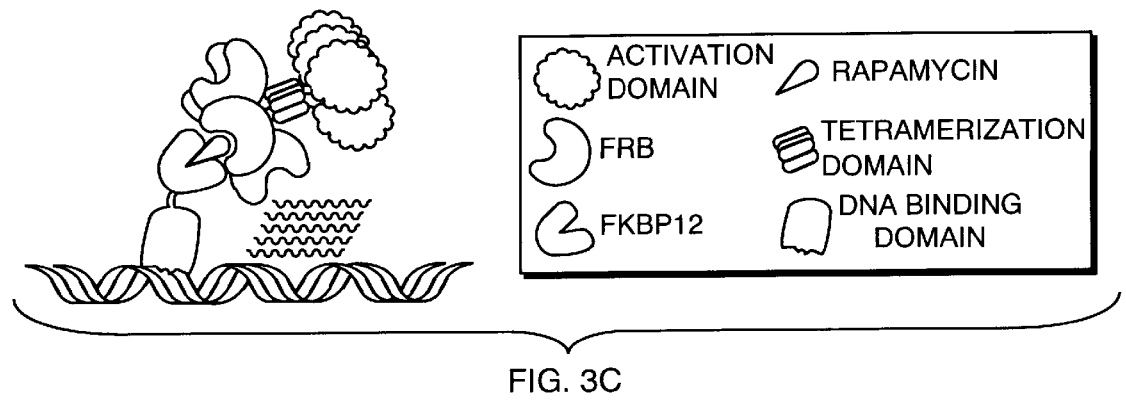
FIG. 3C is a diagrammatic representation of rapamycin-induced dimerization of two fusion proteins, one containing a GAL4 DNA binding domain fused to one copy of FKBP12, and the other containing the "bundled" fusion protein, RLS, which contains the tetramerization domain of lactose repressor between FRB and the p65 activation domain, thereby leading to association of four activation domains with each FKBP in a rapamycin-dependent manner.

Based at least in part on the lack of squelching observed from the instant composite activators, the subject fusion proteins can include one or more oligomerization sequences which permits non-covalent oligomerization of multiple composite activators. For instance, as FIG. 3C shows, including a tetramerization domain permits the formation of multimerized complexes of the composite activator sequences. Reiterating from above, this embodiment derives in part from the discovery that squelching due to abundance of activation tags, particularly for forming the DA complex, is not a hindrance in expression from genomic sequences.

As desired, the composite activation sequence can be provided as part of a fusion protein including a DNA binding domain. In other embodiments, such as illustrated in FIG. 3, the composite activation sequence can be fused with a ligand binding domain which, in the presence of a multivalent ligand, can facilitate recruitment of the composite activator to a DNA-bound complex. The complex can be loaded with multiple activators, in a ligand-dependent manner, by inclusion of multiple ligand binding domains.

In the instance where the composite activator contains one or more oligomerization domains and/or ligand binding domains, but is not contiguous with a DNA binding domain, the composite activator can be coexpressed in cells with a second protein including a DNA binding domain and appropriate oligomerization or ligand binding domains to form complexes with the composite activator proteins. Thus, composite activator proteins can be recruited to a site of transcriptional regulation by interaction with a DNA binding protein by oligomerization, which may be constitutive or inducible.

Techniques for making the subject fusion proteins are adapted from well-known procedures. Essentially, the joining of various DNA fragments coding for different polypeptide sequences is performed in accordance with conventional techniques, employing blunt-ended or stagger-ended termini for ligation, restriction enzyme digestion to provide for appropriate termini, filling in of cohesive ends as appropriate, alkaline phosphatase treatment to avoid undesirable joining, and enzymatic ligation. Alternatively, the fusion gene can be synthesized by conventional techniques including automated DNA synthesizers. In another method, PCR amplification of gene fragments can be carried out using anchor primers which give rise to complementary overhangs between two consecutive gene fragments. Amplification products can subsequently be annealed to generate a chimeric gene sequence (see, for example, Current Protocols in Molecular Biology, Eds. Ausubel et al. John Wiley & Sons: 1992).

A. Activation Tags

The activation tags useful in the composite activators of the present invention can be derived from one or more transcription factors. Polypeptides which can function to activate transcription in eukaryotic cells are well known in the art. In particular, transcriptional activation domains which contain suitable activation tags have been described for many DNA binding proteins and have been shown to retain their activation function when the transcriptional activation domain, or a suitable fragment thereof, is transferred to a heterologous protein.

Activation tags can be naturally occurring or can be synthetic, so long as, either alone or in combination with other activation tags, they are capable of enhancing the efficiency with which the basal and/or activator-dependent transcription complex performs, i.e., so long as they are capable of interacting with a transcription factor or co-activator protein. Any particular activation tag is preferably at least 6 amino acids in length, and preferably contains no more than about 300 amino acid residues, though even more preferably, less than 200 or even less than 100 residues. Naturally occurring activation units include portions of transcription factors, such as a thirty amino acid fragment of the C-terminus of VP16 (amino acids 461–490), referred to herein as "Vc".

Other activation units are derivatives of naturally occurring peptides. For example, the replacement of one amino acid of a naturally occurring activation unit by another may further increase activation. An example of such an activation unit is a derivative of an eight amino acid peptide of VPI6, the derivative having the amino acid sequence (SEQ ID NO:3) DFDLDMLG.

Yet other activation units are entirely synthetic. It is known, for example, that certain random alignments of acidic amino acids are capable of activating transcription. It is well known in the art that certain transcription factors are active only in specific cell types, i.e., that transcription factors can act in a tissue specific manner. Without wanting to be limited to a specific mechanism of action, it is possible that this tissue specificity results from the fact that the transcription factor interacts with specific factors, e.g, cofactors, which are present only in certain cell types. This tissue specificity can be localized to a specific portion of the transcription factor. In certain transcription factors, this portion is located outside activation domains, whereas in other transcription factors, this portion may be localized within an activation domain. Thus, by using activation tags which are functional essentially in specific cells, it is possible to design a transcriptional activator of the invention having a certain tissue specificity. A preferred polypeptide for use in the fusion protein of the invention is the herpes simplex virus virion protein 16 (referred to herein as VP16, the amino acid sequence of which is disclosed in Triezenberg, S. J. et al. (1988) Genes Dev. 2:718–729). In one embodiment, an activation tag corresponding to about 127 of the C-terminal amino acids of VP16 is used. For example, a polypeptide having an amino acid sequence shown in (positions 208–335) can be used as the second polypeptide in the fusion protein. In another embodiment, at least one copy of about 11 amino acids from the C-terminal region of VP16 which retain transcriptional activation ability is used as the activation tag. Preferably, an oligomer of this region (i.e., about 22 amino acids) is used. Suitable C-terminal peptide portions of VP16 are described in Seipel, K. et al. (EMBO J. (1992) 13:4961–4968).

Another example of an acidic activation tag is provided in residues 753–881 of GAL4.

One particularly important source of transcription activation tags which are featured in a number of embodiments of the invention is the (human) NF-kB subunit p65. In one embodiment the chimeric activator contains one or more copies of a peptide sequence comprising all or part of the p65 sequence spanning residues 450–550, or a peptide sequence derived therefrom. In certain embodiments, it has been found that extending the p65 peptide sequence to include sequence spanning p65 residues 361–450, e.g., including the "AP activation tag", leads to an unexpected increase in transcription activation. Moreover, a peptide sequence comprising all or a portion of p65(361–550), or peptide sequence derived therefrom, in combination with heterologous activation tags, can yield surprising additional increases in the level of transcription activation. p65-based activation domains function across a broad range of promoters and have yielded increases in transcription levels six-fold, eight-fold and even 14–15-fold higher than obtained with tandem copies of VP16 which itself is widely recognized as a very potent activation domain.

While the resultant increases in activation potency are dramatic, p65-based transcription factors possess additional and unexpected characteristics. For instance, unlike VP16, the subject p65-based activators do not appear to be toxic to the engineered cells. This is clearly of profound practical significance in many applications. It is expected that recombinant DNA molecules encoding chimeric proteins which contain a p65 activation tag, or peptide sequence derived therefrom, will provide significant advantages for heterologous gene expression in its various contexts, including constitutive systems such as described herein, as well as in regulated systems such as described in International patent applications PCT/US94/01617, PCT/US95/10591, PCT/US96/09948 and the like, as well as in other heterologous transcription systems such as those involving tetracyclin-based based regulation reported by Bujard et al. and those involving steroid or other hormone-based regulation.

One class of p65-based transcription factors contain more than one copy of a p65-derived domain. Such proteins will typically contain two to about six copies of a peptide sequence comprising all or a portion of p65(361–550), or peptide sequence derived therefrom.

Other polypeptides with transcriptional activation ability in eukaryotic cells can be used to provide activation tags for the fusion protein of the invention. Transcriptional activation domains found within various proteins have been grouped into categories based upon similar structural features. Types of transcriptional activation domains include, in addition to the acidic transcription activation domains, proline-rich transcription activation domains, serine/threonine-rich transcription activation domains and glutamine-rich transcription activation domains. Examples of proline-rich activation domains include amino acid residues 399–499 of CTF/NF1 and amino acid residues 31–76 of AP2. Examples of serine/threonine-rich transcription activation domains include amino acid residues 1–427 of ITF1 and amino acid residues 2–451 of ITF2. Examples of glutamine-rich activation domains include amino acid residues 175–269 of Oct1 and amino acid residues 132–243 of Sp1. The amino acid sequences of each of the above described regions, and of other useful transcriptional activation domains, are disclosed in Seipel, K. et al. (EMBO J. (1992) 13:4961–4968).

Still other illustrative activation domains and motifs of human origin include the activation domain of human CTF, the 18 amino acid (SEQ ID NO:4). (NFLQLPQQTQGALLTSQP) glutamine rich region of Oct-2, the N-terminal 72 amino acids of p53, the SYGQQS repeat (SEQ ID NO:5) in Ewing sarcoma gene and an 11 amino acid (535–545) acidic rich region of Rel A protein.

In addition to previously described transcriptional activation domains, novel transcriptional activation tags, which can be identified by standard techniques, are within the scope of the invention. The transcriptional activation ability of a polypeptide can be assayed by linking the polypeptide to another polypeptide having DNA binding activity and determining the amount of transcription of a target sequence that is stimulated by the fusion protein. For example, a standard assay used in the art utilizes a fusion protein of a putative activation tag and a GAL4 DNA binding domain (e.g., amino acid residues 1–93). This fusion protein is then used to stimulate expression of a reporter gene linked to GAL4 binding sites (see e.g., Seipel, K. et al. (1992) EMBO J. 11:4961–4968 and references cited therein).

As set out above, transcriptional activators can also comprise activation tags, which in the absence of other activation tags are incapable of activating transcription. For example, the activation tag AP from VP16 does not activate transcription in the absence of other activation units, even when present in multiple copies.

Accordingly, the invention provides an AP activation tag, or derivative thereof, which may interact with TFIIA, but which on its own is incapable of activating transcription. In one embodiment, the AP polypeptide has the amino acid sequence of residues 361–450 of SEQ ID NO.2, or a fragment thereof. Functionally equivalent derivatives of the AP activation tag can be obtained, for instance, by screening derivatives of AP for binding to TFIIA and measuring transcriptional activity of such a derivative in a co-transfection assay, as described above. Such equivalents are expected to include forms of the activation tag which are tuncated at either the N-terminus or C-terminus or both, e.g., fragments of p65 (or homologous sequences thereto) which are about 75, 60, 50, 30 or even 20 amino acid residues in length (e.g., ranging in length from 20–89 amino acids). Likewise, it is expected that the AP activation tag sequence from p65 can tolerate amino acid substitutions, e.g., to produce AP tags of at least 95%, 90%, 80% and even 70% identity with the AP activation tag sequence of SEQ ID No. 2.

The multiple activation units and other domains of the transcriptional of the invention can be from any eukaryotic species, and it is not necessary that every unit or domain be from the same species. Preferred species include vertebrates, such as mammals. Even more preferred units or domains are from humans. For use of the transcriptional activators of the invention in gene therapy in a subject of a specific species, e.g., human, it is preferable to use units and domains from the same species to avoid immune reactions against the transcriptional activator or complex.

The activation units of a transcriptional coactivator can be covalently linked to each other in a linear array, i.e., the NH2-terminus of one activation unit is linked to the COOH-terminus of another activation unit. The activation units can be arranged in any order. However, as described herein, it has been observed, that certain arrangements of activation units results in higher levels of transcriptional activation than other arrangements. The order in which the activation units should be arranged will depend on the result desired, i.e., the degree of transactivation that one desires to achieve, and can be determined, e.g., by performing cotransfection experiments, as described in the Examples. Briefly, expression vector encoding the activation units in various arrangements linked to a DNA binding domain are cotransfected together with a reporter construct containing a reporter gene operably linked to a promoter containing a DNA site recognized by the DNA binding domain, and expression of the reporter gene is measured. For such assays, it is preferable to use a cell line in which the activation units are known to be active.

In order to optimize the transcriptional activity of a composite activator of the subject invention, it can be advantageous to shuffle the activation tags relative to one another in polypeptide. There are a variety of combinatorial techniques available which can be adapted for creating combinatorial libraries of the subject composite activators by creating and sampling libraries of proteins in which the activation tags are shuffled in the polypeptide to some degree relative to one another.

In an exemplary embodiment, the coding sequences for individual activation tags are synthesized to include a NotI cleavage site at both the 5' and 3' end by addition of the sequence GCGGCCGCN, which also encodes (Ala)3, an unstructured linker. The benefits of unstructured linkers are described below. A variety of nucleic acids encoding such activation tag sequences can be treated with NotI, admixed with one another, and religated to form a combinatorial library representing various positional combinations of the different activation tag sequences relative to each other. Those combination(s) of activation tags producing the greatest level of transcriptional activation can be readily identified in the resulting combinatorial library, e.g., by selections based on expression of a quantifiable reporter gene.

In another embodiment, combinatorial intron splicing can be used to generate a diverse library of composite activation sequences. U.S. Pat. No. 5,498,531 describes a means for carrying out the equivalent of "exon shuffling" by intron-mediated trans-splicing. Briefly, the trans-splicing system of the '531 patent provides an active set of transcripts for trans-splicing wherein flanking intronic sequences can interact in an intermolecular reaction to reconstitute a reactive complex which promotes transesterification of two or more transcripts. RNA transcripts are derived which include an "exon" sequence, e.g., encoding an activation tag, which is flanked on each side by intron sequences that can direct trans-splicing of the exon sequences to each other. By admixing these RNA constructs, intermolecular complementation between the flanking intron sequences of two different constructs forms a functional intron which mediates the transesterification reactions necessary to ligate two discontinuous activation tag sequences to one another, and thereby generate a elongated transcript comprising these concatenated RNA sequences encoding activation tag sequence. In one embodiment, the activation tag "exons" are flanked by portions of one of a group I or group II intron, such that the interaction of the flanking intronic sequences is sufficient to produce an autocatalytic core capable of driving ligation of the exons in the absence of any other factors. In the present context, the term "exon" merely denotes nucleic acid sequences encoding polypeptides including an activation tag, and can, for instance, correspond to naturally and non-naturally occurring exon sequences. The resulting RNA transcripts are reverse transcribed, and as above, the positional permutations of greatest transcriptional activity are easily isolated.

B. DNA Binding Domain

In certain embodiments of the invention, the composite activator is provided as part of a chimeric protein which further comprises a DNA-binding domain. In other embodiments, the composite activator is localized to a DNA sequence by virture of a constitutive or inducible oligomerization with chimeric DNA binding domain. In such instances, the DNA binding domain can be provided in a fusion protein which one or more oligomerization domains or ligand binding domains. The choice of component DNA-binding domains may be influenced by a number of considerations, including the species, system and cell type to which is targeted; the feasibility of its incorporation into a chimeric protein, as may be shown by modeling; and the desired application or utility.

The DNA binding domain can be a naturally occurring DNA-binding domain from a transcription factor. Alternatively, the DNA binding domain can be an artificial (or partially artificial) polypeptide sequence having DNA binding activity. For example, the DNA-binding domain can be a naturally occurring DNA binding domain that has been modified to recognize a different DNA binding site. The particular DNA-binding domain chosen will depend on the target promoter. For example, if the gene to be transcriptionally activated by the subject method is an endogenous gene, the DNA-binding domain must be able to interact with the promoter of the endogenous gene (endogenous promoter). Alternatively, as described in greater detail below, the endogenous promoter could be replaced, e.g., by homologous recombination, with a heterologous promoter for which the DNA binding domain is selected. Such a substitution may be necessary if no transcription factor is known to bind the endogenous promoter of interest. Alternatively, in such a situation, it is also possible to clone a DNA-binding domain interacting specifically with a sequence in the promoter of interest. This can be done, e.g., by phage display screening with a DNA molecule comprising at least a portion of the promoter of interest.

Desirable properties of DNA binding domains include high affinity for specific nucleotide sequences, termed herein "target sequences", low affinity for most other sequences in a complex genome (such as a mammalian genome), low dissociation rates from specific DNA sites, and novel DNA recognition specificities distinct from those of known natural DNA-binding proteins. Preferably, binding of a DNA-binding domain to a specific target sequence is at least two, more preferably three and even more preferably more than four orders of magnitude greater than binding to any one alternative DNA sequence, as may be measured by relative Kd values or by relative rates or levels of transcription of genes associated with the selected and any alternative DNA sequences. It is also preferred that the selected DNA sequence be recognized to a substantially greater degree by the DNA binding domain of the trancriptional activator of the invention than by an endogenous protein. Thus, for example, target gene expression in a cell is preferably two, more preferably three, and even more preferably more than four orders of magnitude greater in the presence of the transcriptional activator of the invention containing a DNA-binding region than in its absence.

Preferred DNA binding domains have a dissociation constant for a target sequence below $10^{-8}$ M, preferably $10^{-9}$ M, more preferably below $10^{-10}$ M, even more preferably below $10^{11}$ M. For gene therapy applications, they are preferably derived from human proteins.

From a structural perspective, DNA-binding that can be used in the invention may be classified as DNA-binding proteins with a helix-turn-helix structural design, such as, but not limited to, Myb, Ultrabithorax, Engrailed, Paired, Fushi tarazu, HOX, Unc86, the Ets and homeobox families of transcription factors, and the previously noted Oct1, Oct2 and Pit; zinc finger proteins, such as Zif268, SWI5, Krüppel and Hunchback; steroid receptors; DNA-binding proteins with the helix-loop-helix structural design, such as Daughterless, Achaete-scute (T3), MyoD, E12 and E47; and other helical motifs like the leucine-zipper, which includes GCN4, C/EBP, c-Fos/c-Jun and JunB. The amino acid sequences of the component DNA-binding domains may be naturally-occurring or non-naturally-occuring (or modified). DNA-binding domains and their target sites can be found at TF SEARCH (http://www.genome.ad:jp/SIT/TFSEARCH html). Another publicly available database of transcription factors and the sequences to which they bind is available from the National Library of Medicine in the "Transcription Data Base".

One strategy for obtaining component DNA-binding domains with properties suitable for this invention is to modify an existing DNA-binding domain to reduce its affinity for DNA into the appropriate range. For example, a homeodomain such as that derived from the human transcription factor Phox 1, may be modified by substitution of the glutamine residue at position 50 of the homeodomain. Substitutions at this position remove or change an important point of contact between the protein and one or two base pairs of the 6-bp DNA sequence recognized by the protein. Thus, such substitutions reduce the free energy of binding and the affinity of the interaction with this sequence and may or may not simultaneously increase the affinity for other sequences. Such a reduction in affinity is sufficient to effectively eliminate occupancy of the natural target site by this protein when produced at typical levels in mammalian cells. But it would allow this domain to contribute binding energy to and therefore cooperate with a second linked DNA-binding domain. Other domains that amenable to this type of manipulation include the paired box, the zinc-finger class represented by steroid hormone receptors, the myb domain, and the ets domain.

In another embodiment, the DNA binding domain is created from the assembly of DNA binding domains from various transcription factors, resulting in a DNA binding domain having a novel DNA binding specificity. Such DNA binding domains, referred to herein as "composite DNA binding domains" can be designed to specifically recognize unique binding sites. For example, a DNA binding domain can be constructed that comprises DNA binding regions from a zinc finger protein and a homeobox protein. One such DNA binding domain is ZFHD1, a composite DNA binding domain comprising an Oct-1 homeodomain and zinc fingers 1 and 2 of Zif268, which is further described in PCT Application WO 96/20951 by Pomerantz et al.

The DNA sequences recognized by a chimeric protein containing a composite DNA-binding domain can be determined experimentally, as described below, or the proteins can be manipulated to direct their specificity toward a desired sequence. A desirable nucleic acid recognition sequence consists of a nucleotide sequence spanning at least ten, preferably eleven, and more preferably twelve or more bases. The component binding portions (putative or demonstrated) within the nucleotide sequence need not be fully contiguous; they may be interspersed with "spacer" base pairs that need not be directly contacted by the chimeric protein but rather impose proper spacing between the nucleic acid subsites recognized by each module. These sequences should not impart expression to linked genes when introduced into cells in the absence of the engineered DNA-binding protein.

To identify a nucleotide sequence that is recognized by a transcriptional activator protein containing the composite DNA-binding region, preferably recognized with high affinity (dissociation constant $10^{-11}$ M or lower are especially preferred), several methods can be used. If high-affinity binding sites for individual subdomains of the composite DNA-binding region are already known, then these sequences can be joined with various spacing and orientation and the optimum configuration determined experimentally (see below for methods for determining affinities). Alternatively, high-affinity binding sites for the protein or protein complex can be selected from a large pool of random DNA sequences by adaptation of published methods (Pollock, R. and Treisman, R., 1990, A sensitive method for the determination of protein-DNA binding specificities. Nucl. Acids Res. 18, 6197–6204). Bound sequences are cloned into a plasmid and their precise sequence and affinity for the proteins are determined. From this collection of sequences, individual sequences with desirable characteristics (i.e., maximal affinity for composite protein, minimal affinity for individual subdomains) are selected for use. Alternatively, the collection of sequences is used to derive a consensus sequence that carries the favored base pairs at each position. Such a consensus sequence is synthesized and tested (see below) to confirm that it has an appropriate level of affinity and specificity.

A number of well-characterized assays are available for determining the binding affinity, usually expressed as dissociation constant, for DNA-binding proteins and the cognate DNA sequences to which they bind. These assays usually require the preparation of purified protein and binding site (usually a synthetic oligonucleotide) of known concentration and specific activity. Examples include electrophoretic mobility-shift assays, DNaseI protection or "footprinting", and filter-binding. These assays can also be used to get rough estimates of association and dissociation rate constants. These values may be determined with greater precision using a BlAcore instrument. In this assay, the synthetic oligonucleotide is bound to the assay "chip," and purified DNA-binding protein is passed through the flow-cell. Binding of the protein to the DNA immobilized on the chip is measured as an increase in refractive index. Once protein is bound at equilibrium, buffer without protein is passed over the chip, and the dissociation of the protein results in a return of the refractive index to baseline value. The rates of association and dissociation are calculated from these curves, and the affinity or dissociation constant is calculated from these rates. Binding rates and affinities for the high affinity composite site may be compared with the values obtained for subsites recognized by each subdomain of the protein. As noted above, the difference in these dissociation constants should be at least two orders of magnitude and preferably three or greater.

The invention further provides composite activators of the present invention provided as a fusion protein with an inducible DNA binding domain(s). In one embodiment, the inducible DNA binding domain is the *E. coli* tet repressor (TetR), which binds to tet operator (tetO) sequences upstream of target genes. In the presence of tetracycline, or an analog, which bind to tetR, DNA binding is abolished and thus transactivation is abolished. This system, in which the TetR had previously been linked to transcription activation domains, e.g., from VP16, is generally referred to as an allosteric "off-switch" described by Gossen and Bujard (Proc. Natl. Acad. Sci. U.S.A. (1992) 89:5547) and in U.S. Pat. Nos. 5,464,758; 5,650,298; and 5,589,362 by Bujard et al. Furthermore, depending on the concentration of the antibiotic in the culture medium (0–1 mu g/ml), target gene expression can be regulated over concentrations up to several orders of magnitude. Thus, the system not only allows differential control of the activity of an individual gene in eukaryotic cells but also is suitable for creation of "on/off" situations for such genes in a reversible way. This system provides very low background and relatively high target gene expression in the absence of tetracycline or an analog. Thus, the invention described herein provides a method for obtaining even stronger transcriptional induction of a target gene, which is regulatable by the tetracycline system or other inducible DNA binding domain. For example, a TetR can be linked to a multiplicity of transcription activation units, such that high levels of transcription occur in the absence of tetracycline or analog thereof and that transcription is repressed in the presence of tetracycline.

In another embodiment, a "reverse" Tet system is used, again based on a DNA binding domain that is a mutant of the *E. coli* TetR, but which binds to TetO in the presence of Tet. Thus, the invention described herein provides a method for obtaining even stronger transcriptional induction of a target gene in the presence of tetracycline or an analog thereof from a very low background in the absence of tetracycline.

C. Oligomerization Domains

As set out above, in various embodiments of the composite activators, the fusion proteins can also include at least one oligomerization domain. Such a domain can be a constitutive oligomerization domain, or an inducible oligomerization domain, i.e., a domain mediating oligomerization only in the presence of a third molecule, such as a small organic molecule. Examples of constitutive oligomerization domains include leucine zippers.

Example of inducible oligomerization domains include FK506 and cyclosporin binding domains of FK506 binding proteins and cyclophilins, and the rapamycin binding domain of FRAP (tori). Such inducible oligomerization domains are referred to herein as "ligand binding domains" and are further described herein under the section entitled accordingly.

In one embodiment of the invention, at least one activation tag or ligand binding domain or DNA binding domain is linked to a constitutive oligomerization domain, e.g., a dimerization or tetramerization domain. A dimerization domain is defined herein as a sequence of amino acids capable of forming homodimers or heterodimers. One example of a dimerization domain is the leucine zipper (LZ) element. Leucine zippers have been identified, generally, as stretches of about 35 amino acids containing 4–5 leucine residues separated from each other by six amino acids (Maniatis and Abel (1989) Nature 341:24–25). Exemplary leucine zippers occur in a variety of eukaryotic DNA binding proteins, such as GCN4, C/EBP, c-Fos, c-Jun, c-Myc and c-Max. Other dimerization domains include helix-loop-helix domains (Murre, C. et al. (1989) Cell 58:537–544). Dimerization domains may also be selected from other proteins, such as the retinoic acid receptor, the thyroid hormone receptor or other nuclear hormone receptors (Kurokawa et al. (1993) Genes Dev. 7:1423–1435) or from the yeast transcription factors GAL4 and HAP1 (Marmonstein et al. (1992) Nature 356:408–414; Zhang et al. (1993) Proc. Natl. Acad. Sci. USA 90:2851–2855). Dimerization domains are further described in U.S. Pat. No. 5,624,818 by Eisenman.

In another embodiment, the oligomerization domain is a tetramerization domain. For example, four activation units can be linked to a single DNA binding domain or a ligand binding domain by covalently linking the activation units to a tetramerization domain. In a preferred embodiment, the tetramerization domain is the E. coli lactose repressor tetramerization domain (amino acids 46–360; Chakerian et al. (1991) J. Biol. Chem. 266:1371; Alberti et al. (1993) EMBO J. 12:3227; and Lewis et al. (1996) Nature 271:1247), as described in the Examples. Thus, the inclusion of a tetramerization domain in a transcriptional activator allows four activation domains to be complexed together and form a transcriptional activator complex. Furthermore, more than one activation unit can be linked to one tetramerization domain, to thereby form a transcriptional activator complex comprising more than 4 activation units.

In another embodiment, the tetramerization domain is that from a p53 protein. The p53 tetramerization domain maps to residues 322–355 of p53 (Wang et al. (1994) Mol. Cell. Biol. 14:5182; Clore et al. (1994) Science 265:386) and is further described in U.S. Pat. No. 5,573,925 by Halazonetis.

The invention also provides for transcriptional activators containing at least one modified oligomerization domain. Modifications in the oligomerization domain may increase the stability of tetramer formation, for example, substitutions that stabilize oligomerization driven by leucine zippers are known (Krylov et al. (1994) cited above; O'Shea et al. (1992) cited above). As an exemplary modification of this type, residues 174 or 175 of human p53 are substituted by glutamine or leucine, respectively, in a p53 chimeric protein of this invention.

In other embodiments, the oligomerization domain can be an altered p53 tetramerization domain which is incapable of forming hetero-tetramers with p53 proteins that have a wild-type p53 tetramerization domain, such as wild-type p53 or tumor-derived p53 mutants. Such altered p53 tetramerization domains are further described in U.S. Pat. No. 5,573,925 by Halazonetis.

These altered p53 tetramerization domains are characterized by disruption of the native p53 tetramerization domain and insertion of a heterologous oligomerization domain in a way that preserves tetramerization. According to this invention, a disruption of the p53 tetramerization domain, involving residues 335–348 or a subset of these residues, sufficiently disrupts the function of this domain so that it can no longer drive tetramerization with wild-type p53 or tumor-derived p53 mutants. At the same time, however, introduction of a heterologous dimerization domain reestablishes the ability to form tetramers, which is mediated both by the heterologous dimerization domain and by the residual tetramerization domain of p53.

Other exemplary suitable tetramerization domains include artificial tetramerization domains, such as variants of the GCN4 leucine zipper that form tetramers (Alberti et al. (1993) EMBO J. 12:3227–3236; Harbury et al. (1993) Science 262:1401–1407; Krylov et al. (1994) EMBO J. 13:2849–2861). One of skill in the art could readily select alternate tetramerization domains. For example, the tetrameric variant of GCN4 leucine zipper described in Harbury et al. (1993), supra, has isoleucines at positions d of the coiled coil and leucines at positions a, in contrast to the original zipper which has leucines and valines, respectively.

The GCN4 leucine zipper drives parallel subunit assembly [Harbury et al. (1993), cited above], while the native p53 tetramerization domain drives antiparallel assembly [Clore et al. (1994) cited above; Sakamoto et al. (1994) Proc. Natl. Acad. Sci. USA 91:8974–8978]. Thus, various conformations of activation unit complexes can be obtained by choosing various tetramerization domains.

In addition, the art also provides a variety of techniques for identifying other naturally occurring oligomerization domains, as well as oligomerization domains derived from mutant or otherwise artificial sequences. See, for example, Zeng et al. (1997) Gene 185:245; O'Shea et al. (1992) Cell 68:699–708; Krylov et al. [cited above].

The distance between the oligomerization domain and other components of the fusion proteins can be varied. In one embodiment, there is no linker between an activation unit and a tetramerization domain, e.g, an altered GCN4 leucine zipper. In other embodiments however, there are glutamic acid or asparagine or isoleucine linkers, respectively. Linkers may be present for cloning convenience or to confer some useful property. For example, residues that stabilize specific secondary structure elements, such as alpha-helices, are known (Richardson et al. (1988) Science 240:1648–1652). Such residues can be introduced in the linkers to stabilize the oligomerization domains. For example the linkers glycine-asparagine, arginine-glycine-asparagine, arginine-glycine-glycine-asparagine-proline-glutamic acid (SEQ ID No:6), glycine-glycine- asparagine-glutamine-alanine (SEQ ID No:7), are all designed to stabilize the N-terminus of the alpha -helical oligomerization domain.

In one embodiment, the chimeric protein comprises an activation unit fused to an asparagine linker and then to a tetrameric variant of GCN4 residues 249–281. Alternatively, the linker can be an arginine-glycine-asparagine linker, an arginine-glycine-glycine-asparagine- proline-glutamic acid linker (SEQ ID No:6), a glycine-glycine-asparagine-glutamine-alanine linker (SEQ ID No:7).

A variety of other amino acid or peptide linkers may be used for the reasons discussed above, provided they do not interfere with the function of the activation units and ligand binding domain or DNA binding domain.

D. Ligand Binding Domain

In another embodiment of the invention, components of the subject system include one or more ligand binding domains for mediating oligomerization of fusion proteins in a ligand-dependent fashion. In a preferred embodiment, the ligand is capable of interacting with two ligand binding domains. In an exemplary embodiment, formation of transcriptional complexes is regulated by addition of a ligand, and comprises introducing into the cell a fusion protein including a composite activator and a ligand binding domain, as well as a second fusion protein including a DNA binding domain and a ligand binding domain, such that in the presence of the ligand, a transcriptional activator complex is formed between the two fusion proteins. Preferred ligands include macrolides such as rapamycin, cyclosporin A, FK506, FK1012, and analogs thereof, and other synthetic dimerizers or oligomerizers. Ligand binding domains include the FK506 binding domain of FKBP, the cyclosporin-binding domain of calcineurin, and the rapamycin-binding domain of FRAP. These binding domains and ligands are further disclosed, e.g., in PCT/US93/01617. Such fusion proteins permit control of the expression of a target gene to be dependent on addition of an appropriate ligand, e.g., one which is capable of interacting simultaneously with the two ligand binding domains.

In general, the ligand binding domain of a chimeric protein of this invention can be any convenient domain which will allow for ligand-dependent oligomerization of fusion proteins using a natural or unnatural ligand, preferably an unnatural synthetic ligand. Of particular interest are binding proteins for which ligands (preferably small organic ligands) are known or may be readily produced. These receptors or ligand binding domains include the FKBPs and cyclophilin receptors, the steriod receptors, the tetracycline receptor, the other receptors indicated above, and the like, as well as "unnatural" receptors, which can be obtained from antibodies, particularly the heavy or light chain subunit, mutated sequences thereof, random amino acid sequences obtained by stochastic procedures, combinatorial syntheses, and the like.

For the most part, the receptor domains will be at least about 50 amino acids, and fewer than about 350 amino acids, usually fewer than 200 amino acids, either as the natural domain or truncated active portion thereof. Preferably the binding domain will be small (<25 kDa, to allow efficient transfection in viral vectors), monomeric (this rules out the avidin-biotin system), nonimmunogenic, and should have synthetically accessible, cell permeable, nontoxic ligands that can be configured for dimerization.

Multimerizing ligands useful in practicing this invention are multivalent, i.e., capable of binding to, and thus multimerizing, two or more of chimeric protein molecules having a ligand binding domain. The multimerizing ligand may bind to the proteins containing such ligand-binding domains, in either order or simultaneously, preferably with a Kd value below about $10^{-6}$, more preferably below about $10^{-7}$, even more preferably below about $10^{-8}$, and in some embodiments below about $10^{-9}$ M. The ligand preferably is not a protein or polypeptide and has a molecular weight of less than about 5 kDa, preferably below 2 kDa. The ligand-binding domains of the chimeric proteins so multimerized may be the same or different. Ligand binding domains include among others, various immunophilin domains. One example is the FKBP domain which is capable of binding to dimerizing ligands incorporating FK506 moieties or other FKBP-binding moieties. See e.g. PCT/US93/01617, the full contents of which are hereby incorporated by reference.

The portion of the construct encoding the ligand binding domain can be subjected to mutagenesis for a variety of reasons. The mutagenized domain can provide for higher binding affinity, allow for discrimination by a ligand between the mutant and naturally occurring forms of the ligand binding domain, provide opportunities to design a ligand-ligand binding domain pairs, or the like. The change in the ligand binding domain can involve changes in amino acids known to be at the binding site, random mutagenesis using combinatorial techniques, where the codons for the amino acids associated with the binding site or other amino acids associated with conformational changes can be subject to mutagenesis by changing the codon(s) for the particular amino acid, either with known changes or randomly, expressing the resulting proteins in an appropriate prokaryotic host and then screening the resulting proteins for binding. Illustrative of this situation is to modify FKBP 12's Phe36 to Ala and/or Asp37 to Gly or Ala to accommodate a substituent at positions 9 or 10 of FK506 or FK520. In particular, mutant FKBP 12 moieties which contain Val, Ala, Gly, Met or other small amino acids in place of one or more of Tyr26, Phe36, Asp37, Tyr82 and Phe99 are of particular interest as receptor domains for FK506-type and FK-520-type ligands containing modifications at C9 and/or C10.

Illustrative examples of rapamycin-binding domains are those which include an approximately 89-amino acid rapamycin-binding domain from FRAP, e.g., containing residues 2025–2113 of human FRAP. Similar considerations apply to the generation of mutant FRAP-derived domains which bind preferentially to rapamycin analogs (rapalogs) containing modifications (i.e., are 'bumped') relative to rapamycin in the FRAP-binding effector domain. For example, one may obtain preferential binding using rapalogs bearing substituents other than —OMe at the C7 position with FRBs based on the human FRAP FRB peptide sequence but bearing amino acid substitutions for one of more of the residues Tyr2038, Phe2039, Thr2098, Gln2099, Trp2101 and Asp2102. Exemplary mutations include Y2038H, Y2038L, Y2038V, Y2038A, F2039H, F2039L, F2039A, F2039V, D2102A, T2098A, T2098N, and T2098S. Rapalogs bearing substituents other than —OH at C28 and/or substituents other than =O at C30 may be used to obtain preferential binding to FRAP proteins bearing an amino acid substitution for Glu2032. Exemplary mutations include E2032A and E2032S. Proteins comprising an FRB containing one or more amino acid replacements at the foregoing positions, libraries of proteins or peptides randomized at those positions (i.e., containing various substituted amino acids at those residues), libraries randomizing the entire protein domain, or combinations of these sets of mutants are made using the procedures described above to identify mutant FRAPs that bind preferentially to bumped rapalogs.

Other macrolide binding domains useful in the present invention, including mutants thereof, are described in the art. See, for example, WO96/41865, WO96/13613, WO96/06111, WO96/06110, WO96/06097, WO96/12796, WO95/05389, WO95/02684, WO94/18317, each of which is expressly incorporated by reference herein.

The ability to employ in vitro mutagenesis or combinatorial modifications of sequences encoding proteins allows for the production of libraries of proteins which can be screened for binding affinity for different ligands. For example, one can totally randomize a sequence of 1 to 5, 10 or more codons, at one or more sites in a DNA sequence encoding a binding protein, make an expression construct and introduce the expression construct into a unicellular microorganism, and develop a library. One can then screen the library for binding affinity to one or desirably a plurality of ligands. The best affinity sequences which are compatible with the cells into which they would be introduced can then be used as the ligand binding domain. The ligand would be screened with the host cells to be used to determine the level of binding of the ligand to endogenous proteins. A binding profile could be defined weighting the ratio of binding affinity to the mutagenized binding domain with the binding affinity to endogenous proteins. Those ligands which have the best binding profile could then be used as the ligand. Phage display techniques, as a non-limiting example, can be used in carrying out the foregoing.

In other embodiments, antibody subunits, e.g. heavy or light chain, particularly fragments, more particularly all or part of the variable region, or fusions of heavy and light chain to create single chain antibodies, can be used as the ligand binding domain. Antibodies can be prepared against haptenic molecules which are physiologically acceptable and the individual antibody subunits screened for binding affinity. The cDNA encoding the subunits can be isolated and modified by deletion of the constant region, portions of the variable region, mutagenesis of the variable region, or the like, to obtain a binding protein domain that has the appropriate affinity for the ligand. In this way, almost any physiologically acceptable haptenic compound can be employed as the ligand or to provide an epitope for the ligand. Instead of antibody units, natural receptors can be employed, where the binding domain is known and there is a useful ligand for binding.

In yet another embodiment of the invention, the DNA binding unit is linked to more than one ligand binding domain. For example, a DNA binding domain can be linked to at least 2, 3, 4, or 5 ligand binding domains. A DNA binding domain can also be linked to at least 5 ligand binding domains or any number of ligand binding domains. In such embodiments, the ligand binding domains can be, by illustration, linked to each other in a linear array, by linking the NH2-terminus of one ligand binding domain to the COOH-terminus of another ligand binding domain, e.g., as shown in FIG. 3. Thus, numerous composite activators can be linked to a single DNA binding domain in the presence of a ligand.

The invention further provides additional induction systems. In one embodiment, the invention uses an alternative allosteric on-switch for transcription which employs a deletion mutant of the human progesterone receptor, i.e., which no longer binds progesterone or any known endogenous steroid but can be activated by the orally active progesterone antagonist RU486, described, e.g, in Wang et al. (1994) Proc. Natl. Acad.

Sci. U.S.A. 91:8180. Activation was demonstrated, e.g, in cells transplanted into mice using doses of RU486 (5–50 μg/kg) considerably below the usual dose for inducing abortion in humans (10 mg/kg). however, according to the art describing this system, the induction ratio in culture and in animals was rather low. Applying the invention described herein in this system would provide an inducible system having a higher induction ratio. Thus, the invention provides a transcriptional activator comprising at least one subunit which is covalently linked to a mutant steroid binding domain to yield a transcriptional activator which transactivates in a RU486-dependent manner, resulting in high induction ratios.

The invention can be adapted to an ecdysone inducible system. Early work demonstrated that fusing the Drosophila steroid ecdysone (Ec) receptor (EcR) Ec-binding domain to heterologous DNA binding and activation domains, such as *E. coli* IexA and herpesvirus VP 16 permits ecdysone-dependent activation of target gen es downstream of appropriate binding sites (Christopherson et al. (1992) Proc. Natl. Acad. Sci. U.S.A. 89:6314). An improved ecdysone regulation system has been developed, using the DNA binding domain of the EcR itself. In this system, the regulating transcription factor is provided as two proteins: (1) a truncated, mutant EcR fused to herpes VP16 and (2) the mammalian homolog (RXR) of Ultraspiracle protein (USP), which heterodimerizes with the EcR (No et al. (1996) Proc. Natl. Acad. Sci. U.S.A. 93:3363). In this system, because the DNA binding domain was also recognized by a human receptor (the human farnesoid X receptor), it was altered to a site recognized only by the mutant EcR. Thus, the invention provides an ecdysone inducible system, in which a truncated mutant EcR is fused to at least one subunit of a transcriptional activator of the invention. The transcriptional activator further comprises USP, thereby providing high level induction of transcription of a target gene having the EcR target sequence, dependent on the presence of ecdysone.

The invention can also be applied to any other inducible system, thereby providing an inducible system having a higher ratio of background to induction due to the potent transcriptional activity of the transcriptional activators of the invention.

E. Additional Domains and Linkers

Additional domains may be included in the transcriptional activators of this invention. For example, the transcriptional activators may contain a nuclear localization sequence which provides for the protein to be translocated to the nucleus. Accordingly, in one embodiment of the invention, at least one of the subunits of the transcriptional activator of the invention, e.g., activation unit, DNA binding domain, or ligand binding domain, further comprises a nuclear localization signal (NLS). A NLS can be fused to the N-terminus, or the C-terminus of a subunit, e.g., an activation unit, or can be inserted at the junction of one subunit with another subunit, e.g., between an activation domain and a DNA binding or ligand binding domain or oligomerization domain or elsewhere in the protein, as long as the function of the subunits is not disrupted by insertion of the NLS. Typically a nuclear localization sequence has a plurality of basic amino acids, referred to as a bipartite basic repeat (reviewed in Garcia-Bustos et al. (1991) Biochimica et Biophysica Acta 1071:83–101). The NLS may be that of SV40 large T antigen which is comprised of amino acids proline-lysine-lysine-lysine-arginine-lysine-valine (SEQ ID No:8) (Kalderon et al. (1984) Cell 39:499–509). The NLS may also be from a p53 protein. Wild-type p53 contains three nuclear localization signals (NLS), all of which map to the C-terminus of wild-type p53 and specifically to residues 316–325, 369–375 and 379–384 of p53 (Shaulsky et al. (1990) Mol. Cell. Biol.10:6565–6577). Additional heterologous NLS are described by Shaulsky et al (1990) supra and Shaulsky et al.(1991) Oncogene 6:2056.

The chimeric proteins may include domains that facilitate their purification, e.g. "histidine tags" or a glutathione-S-transferase domain. They may include "epitope tags" encoding peptides recognized by known monoclonal antibodies for the detection of proteins within cells or the capture of proteins by antibodies in vitro.

It may be necessary in some instances to introduce an unstructured polypeptide linker region between an activation tag or tags and other portions of the chimeric activator. Where the fusion protein also includes, for example, oligomerization sequences, it may be preferable to situate the linker between the oligomerization sequences and the activation tags. The linker can facilitate enhanced flexibility of the fusion protein, while the oligomerization sequences are relatively free to make other inter-protein contacts, e.g., with other chimeric activators. The linker can also reduce steric hindrance between any two fragments of the fusion protein. The linker can also facilitate the appropriate folding of each fragment to occur. The linker can be of natural origin, such as a sequence determined to exist in random coil between two domains of a protein. An exemplary linker sequence is the linker found between the C-terminal and N-terminal domains of the RNA polymerase a subunit. Other examples of naturally occurring linkers include linkers found in the lcI and LexA proteins. Alternatively, the linker can be of synthetic origin. For instance, the sequence (SEQ ID No:9) (Gly4Ser)3 can be used as a synthetic unstructured linker. Linkers of this type are described in Iluston et al. (1988) PNAS 85:4879; and U.S. Pat. No. 5,091,513, both incorporated by reference herein.

In some embodiments it is preferable that the design of a linker involve an arrangement of domains which requires the linker to span a relatively short distance, preferably less than about 10 Å. However, in certain embodiments, depending, e.g., upon the selected DNA-binding domains and the configuration, the linker may span a distance of up to about 50 Å.

Within the linker, the amino acid sequence may be varied based on the preferred characteristics of the linker as determined empirically or as revealed by modeling. For instance, in addition to a desired length, modeling studies may show that side groups of certain amino acids may interfere with the biological activity, e.g. DNA binding or transcriptional activation, of the protein. Considerations in choosing a linker include flexibility of the linker, charge of the linker, and presence of some amino acids of the linker in the naturally-occurring subunits. The linker can also be designed such that residues in the linker contact DNA, thereby influencing binding affinity or specificity, or to interact with other proteins. For example, a linker may contain an amino acid sequence which can be recognized by a protease so that the activity of the chimeric protein could be regulated by cleavage. In some cases, particularly when it is necessary to span a longer distance between subunits or when the domains must be held in a particular configuration, the linker may optionally contain an additional folded domain.

Most of the subject fusion proteins can be tested for activity in vivo using a simple assay (F. M. Ausubel et al. Eds. Current Protocols in Molecular Biology, John Wiley & Sons, New York, 1994; de Wet et al. (1987) Mol. Cell Biol. 7:725). The in vivo assay requires an expression construct containing and capable of directing the expression of a recombinant DNA sequence encoding the composite activator, and as appropriate, other proteins required for DNA localization of the activator. The assay also requires a plasmid containing a reporter gene, e.g., the luciferase gene, the chloramphenicol acetyl transferase (CAT) gene, secreted alkaline phosphatase or the human growth hormone (hGH) gene, linked to a binding site for the transcription factor. The expression constructs are introduced into host cells which normally do not produce interfering levels of the reporter gene product. A second group of cells, which lacks the composite activator or the means for localizing the activator to the reporter gene can serve as the control.

The production of mRNA or protein encoded by the reporter gene is measured. An increase in reporter gene expression not seen in the controls indicates that the transcription factor is a positive regulator of transcription. If reporter gene expression is less than that of the control, the transcription factor is a negative regulator of transcription.

Optionally, the assay may include a transfection efficiency control plasmid. This plasmid expresses a gene product independent of the test gene, and the amount of this gene product indicates roughly how many cells are taking up the plasmids and how efficiently the DNA is being introduced into the cells. Additional guidance on evaluating chimeric proteins of this invention is provided below.

III. Nucleic Acid Compositions

In another aspect of the invention, the proteins described herein are provided in expression vectors. For instance, expression vectors are contemplated which include a nucleotide sequence encoding a polypeptide containing a composite activator of the present invention, which coding sequence is operably linked to at least one transcriptional regulatory sequence. Regulatory sequences for directing expression of the instant fusion proteins are art-recognized and are selected by a number of well understood criteria. Exemplary regulatory sequences are described in Goeddel; Gene Expression Technology: Methods in Enzymology, Academic Press, San Diego, Calif. (1990). For instance, any of a wide variety of expression control sequences that control the expression of a DNA sequence when operatively linked to it may be used in these vectors to express DNA sequences encoding the fusion proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the promoter for 3-phosphoglycerate kinase or other glycolytic enzymes, the promoters of acid phosphatase, e.g., Pho5, and the promoters of the yeast a-mating factors and other sequences known to control the expression of genes of prokaryotic or eukaryotic cells or their viruses, and various combinations thereof. It should be understood that the design of the expression vector may depend on such factors as the choice of the host cell to be transformed. Moreover, the vector's copy number, the ability to control that copy number and the expression of any other protein encoded by the vector, such as antibiotic markers, should also be considered.

As will be apparent, the subject gene constructs can be used to cause expression of the subject fusion proteins in cells propagated in culture, e.g. to produce proteins or polypeptides, including fusion proteins, for purification.

This invention also pertains to a host cell transfected with a recombinant gene in order to express one of the subject polypeptides. The host cell may be any prokaryotic or eukaryotic cell. For example, a fusion proteins of the present invention may be expressed in bacterial cells such as $E.$ $coli$, insect cells (baculovirus), yeast, or mammalian cells. Other suitable host cells are known to those skilled in the art.

Accordingly, the present invention further pertains to methods of producing the subject fusion proteins. For example, a host cell transfected with an expression vector encoding a protein of interest can be cultured under appropriate conditions to allow expression of the protein to occur. The protein may be secreted, by inclusion of a secretion signal sequence, and isolated from a mixture of cells and medium containing the protein. Alternatively, the protein may be retained cytoplasmically and the cells harvested, lysed and the protein isolated. A cell culture includes host cells, media and other byproducts. Suitable media for cell culture are well known in the art. The proteins can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the protein.

Thus, a coding sequence for a fusion protein of the present invention can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures.

Expression vehicles for production of a recombinant protein include plasmids and other vectors. For instance, suitable vectors for the expression of the instant fusion proteins include plasmids of the types: pBR322-derived plasmids, pEMBL-derived plasmids, pEX-derived plasmids, pBTac-derived plasmids and pUC-derived plasmids for expression in prokaryotic cells, such as $E.$ $coli$.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al., (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant fusion proteins by the use of a baculovirus expression system. Examples of such baculovirus expression systems include pVL-derived vectors (such as pVL 1392, pVL 1393 and pVL941), pAcUW-derived vectors (such as pAcUW1), and pBlueBac-derived vectors (such as the βgal gal containing pBlueBac III).

In yet other embodiments, the subject expression constructs are derived by insertion of the subject gene into viral vectors including recombinant retroviruses, adenovirus, adeno-associated virus, and herpes simplex virus-1, or recombinant bacterial or eukaryotic plasmids. As described in greater detail below, such embodiments of the subject expression constructs are specifically contemplated for use in various in vivo and ex vivo gene therapy protocols.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a fusion protein of the present invention, e.g., a composite activator, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include SYMBOL 121\f "Symbol" Crip, SYMBOL 121\f "Symbol" Cre, SYMBOL 121\f "Symbol" 2 and SYMBOL 121\f "Symbol" Am. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis et al., (1985) Science 230:1395–1398; Danos and Mulligan, (1988) PNAS USA 85:6460–6464; Wilson et al., (1988) PNAS USA 85:3014–3018; Armentano et al., (1990) PNAS USA 87:6141–6145; Huber et al., (1991) PNAS USA 88:8039–8043; Ferry et al., (1991) PNAS USA 88:8377–8381; Chowdhury et al., (1991) Science 254:1802–1805; van Beusechem et al., (1992) PNAS USA 89:7640–7644; Kay et al., (1992) Human Gene Therapy 3:641–647; Dai et al., (1992) PNAS USA 89:10892–10895; Hwu et al., (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) PNAS USA 86:9079–9083; Julan et al., (1992) J. Gen Virol 73:3251–3255; and Goud et al., (1983) Virology 163:251–254); or coupling cell surface ligands to the viral env proteins (Neda et al., (1991) J. Biol. Chem. 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Another viral gene delivery system useful in the present invention utilizes adenovirus-derived vectors. The genome of an adenovirus can be manipulated such that it encodes a gene product of interest, but is inactivate in terms of its ability to replicate in a normal lytic viral life cycle (see, for example, Berkner et al., (1988) BioTechniques 6:616; Rosenfeld et al., (1991) Science 252:431–434; and Rosenfeld et al., (1992) Cell 68:143–155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) PNAS USA 89:6482–6486), hepatocytes (Herz and Gerard, (1993) PNAS USA 90:2812–2816) and muscle cells (Quantin et al., (1992) PNAS USA 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al., (1979) Cell 16:683; Berkner et al., supra; and Graham et al., in Methods in Molecular Biology, E. J. Murray, Ed. (Humana, Clifton, N.J., 1991) vol. 7. pp. 109–127). Expression of the inserted chimeric gene can be under control of, for example, the E1A promoter, the major late promoter (MLP) and associated leader sequences, the viral E3 promoter, or exogenously added promoter sequences.

Yet another viral vector system useful for delivery of the subject chimeric genes is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. (1992) 158:97–129). It is also one of the few viruses that may integrate its DNA into non-dividing cells, and exhibits a high frequency of stable integration (see for example Flotte et al., (1992) Am. J. Respir. Cell. Mol. Biol. 7:349–356; Samulski et al., (1989) J. Virol. 63:3822–3828; and McLaughlin et al., (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al., (1985) Mol. Cell. Biol. 5:3251–3260 can be used to introduce DNA into cells. A variety of nucleic acids have been introduced into different cell types using AAV vectors (see for example Hermonat et al., (1984) PNAS USA 81:6466–6470; Tratschin et al., (1985) Mol. Cell. Biol. 4:2072–2081; Wondisford et al., (1988) Mol. Endocrinol. 2:32–39; Tratschin et al., (1984) J. Virol. 51:611–619; and Flotte et al., (1993) J. Biol. Chem. 268:3781–3790).

Other viral vector systems that may have application in gene therapy have been derived from herpes virus, vaccinia virus, and several RNA viruses. In particular, herpes virus vectors may provide a unique strategy for persistence of the recombinant gene in cells of the central nervous system and ocular tissue (Pepose et al., (1994) Invest Ophthalmol Vis Sci 35:2662–2666).

In addition to viral transfer methods, such as those illustrated above, non-viral methods can also be employed to cause expression of a protein in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the gene by the targeted cell. Exemplary gene delivery systems of this type include liposomal derived systems, poly-lysine conjugates, and artificial viral envelopes.

In a representative embodiment, a gene encoding a composite activator can be entrapped in liposomes bearing positive charges on their surface (e.g., lipofectins) and (optionally) which are tagged with antibodies against cell surface antigens of the target tissue (Mizuno et al., (1992) No Shinkei Geka 20:547–551; PCT publication WO91/06309; Japanese patent application 1047381; and European patent publication EP-A-43075). For example, lipofection of neuroglioma cells can be carried out using liposomes tagged with monoclonal antibodies against glioma-associated antigen (Mizuno et al., (1992) Neurol. Med. Chir. 32:873–876).

In yet another illustrative embodiment, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, any of the subject gene constructs can be used to transfect specific cells in vivo using a soluble polynucleotide carrier comprising an antibody conjugated to a polycation, e.g. poly-lysine (see U.S. Pat. 5,166,320). It will also be appreciated that effective delivery of the subject nucleic acid constructs via -mediated endocytosis can be improved using agents which enhance escape of the gene from the endosomal structures. For instance, whole adenovirus or fusogenic peptides of the influenza IIA gene product can be used as part of the delivery system to induce efficient disruption of DNA-containing endosomes (Mulligan et al., (1993) Science 260–926; Wagner et al., (1992) PNAS USA 89:7934; and Christiano et al., (1993) PNAS USA 90:2122).

In clinical settings, the gene delivery systems can be introduced into a patient by any of a number of methods, each of which is familiar in the art.

For instance, a pharmaceutical preparation of the gene delivery system can be introduced systemically, e.g. by intravenous injection, and specific transduction of the construct in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al., (1994) PNAS USA 91:3054–3057).

IV. Target Gene

As used herein, the term "target gene" refers to a gene, whose transcription is stimulated according to the method of the invention. In a preferred embodiment, the gene is integrated in the chromosomal DNA of a cell. A cell comprising a target gene is referred to herein as a "target cell".

In a preferred embodiment of the invention, the target gene is an endogenous gene. As used herein, the term "endogenous gene" refers to a gene which is naturally present in a cell, in its natural environment, i.e., not a gene which has been introduced into the cell by genetic engineering. The endogenous gene can be any gene having a promoter that is recognized by at least one transcription factor. In a preferred embodiment, the promoter or any regulatory element thereof, of the endogenous gene ("endogenous promoter" and "endogenous regulatory element", respectively), is recognized by a known, preferably cloned, DNA binding protein, whether it is a transcriptional activator or repressor. Alternatively, if no DNA binding protein is known to interact with a target promoter, it is possible to clone such a factor using techniques well known in the art without undue experimentation, such as screening of expression libraries with at least a portion of the target promoter. Furthermore, the affinity of binding of a DNA binding domain to a target sequence can be improved according to methods known in the art. Such methods comprise, e.g., introducing mutations into the DNA binding domain and screening for mutants having increased DNA binding affinity.

In another embodiment of the invention, the target gene is an endogenous gene, which contains an exogenous target sequence. The exogenous target sequence can be inserted into the endogenous promoter or substitute at least a portion of the endogenous promoter. In preferred embodiments, the exogenous promoter or regulatory element introduced into the endogenous target promoter is recognized by a DNA binding protein, capable of binding with high affinity and specificity to a target sequence. In a preferred embodiment, the DNA binding protein is human. However, the DNA binding protein can be from any other species. For example, the DNA binding protein can be from the yeast GAL4 protein.

In yet another embodiment, the target gene is an exogenous gene. In a preferred embodiment, the exogenous gene is integrated into the chromosomal DNA of a cell. The exogenous gene can be inserted into the chromosomal DNA, or the exogenous gene can substitute for at least a portion of an endogenous gene. The target gene can be present in a single copy or in multiple copies. In view of the experimental results described herein, it is not necessary that the target gene be present in more than one copy. However, if even higher levels of protein encoded by the target gene is desired, multiple copies of the gene can be used.

In one embodiment, the taget gene construct enables transcription of a target gene to be regulated by a transcription factor in accordance with this invention comprises a DNA molecule which includes a synthetic transcription unit typically consisting of: (1) one copy or multiple copies of a DNA sequence recognized with high-affinity by the DNA binding domain of a fusion protein which includes a composite activator, or of a protein which recruits the composite activator; (2) a promoter sequence consisting minimally of a TATA box and initiator sequence but optionally including other transcription factor binding sites; (3) a coding sequence for a desired gene product, including sequences that promote the initiation and termination of translation, if appropriate; (4) an optional sequence consisting of a splice donor, splice acceptor, and intervening intron DNA; and (5) a sequence directing cleavage and polyadenylation of the resulting RNA transcript. A wide variety of genes can be employed as the target gene, including genes that encode a therapeutic protein, antisense sequence or ribozyme of interest. The target gene can be any sequence of interest which provides a desired phenotype. It can encode a surface membrane protein, a secreted protein, a cytoplasmic protein, or there can be a plurality of target genes encoding different products. The target gene may be an antisense sequence which can modulate a particular pathway by inhibiting a transcriptional regulation protein or turn on a particular pathway by inhibiting the translation of an inhibitor of the pathway. The target gene can encode a ribozyme which may modulate a particular pathway by interfering, at the RNA level, with the expression of a relevant transcriptional regulator or with the expression of an inhibitor of a particular pathway. The proteins which are expressed, singly or in combination, can involve homing, cytotoxicity, proliferation, immune response, inflammatory response, clotting or dissolving of clots, hormonal regulation, etc. The proteins expressed may be naturally-occurring proteins, mutants of naturally-occurring proteins, unique sequences, or combinations thereof.

Various secreted products include hormones, such as insulin, human growth hormone, glucagon, pituitary releasing factor, ACTH, melanotropin, relaxin, etc.; growth factors, such as EGF, IGF-1, TGF-$\alpha$, -$\beta$, PDGF, G-CSF, M-CSF, GM-CSF, FGF, erythropoietin, thrombopoietin, megakaryocytic stimulating and growth factors, etc.; interleukins, such as IL-1 to -13; TNF-$\alpha$ and -$\beta$, etc.; and enzymes and other factors, such as tissue plasminogen activator, members of the complement cascade, perforins, superoxide dismutase, coagulation factors, antithrombin-III, Factor VIIIc, Factor VIIIvW, Factor IX, $\alpha$-antitrypsin, protein C, protein S, endorphins, dynorphin, bone morphogenetic protein, etc.

The gene can encode a naturally-occurring surface membrane protein or a protein made so by introduction of an appropriate signal peptide and transmembrane sequence. Various such proteins include homing receptors, e.g. L-selectin (Mel-14), blood-related proteins, particularly having a kringle structure, e.g. Factor VIIIc, Factor VIIIvW, hematopoietic cell markers, e.g. CD3, CD4, CD8, B-cell receptor, TCR subunits ($\alpha,\beta,\gamma,\delta$, CD10, CD19, CD28, CD33, CD38, CD41, etc., receptors, such as the interleukin receptors IL-2R, IL-4R, etc., channel proteins for influx or efflux of ions, e.g. Ca+2, K+, Na+, Cl- and the like; CFTR, tyrosine activation motif, zap-70, etc.

Proteins may be modified for transport to a vesicle for exocytosis. By adding the sequence from a protein which is directed to vesicles, where the sequence is modified proximal to one or the other terminus, or situated in an analogous position to the protein source, the modified protein will be directed to the Golgi apparatus for packaging in a vesicle. This process in conjunction with the presence of the chimeric proteins for exocytosis allows for rapid transfer of the proteins to the extracellular medium and a relatively high localized concentration.

Also, intracellular proteins can be of interest, such as proteins in metabolic pathways, regulatory proteins, steroid receptors, transcription factors, etc., depending upon the nature of the host cell. Some of the proteins indicated above can also serve as intracellular proteins.

By way of further illustration, in T-cells, one may wish to introduce genes encoding one or both chains of a T-cell receptor. For B-cells, one could provide the heavy and light chains for an immunoglobulin for secretion. For cutaneous cells, e.g. keratinocytes, particularly stem cell keratinocytes, one could provide for protection against infection, by secreting ($\alpha$-, $\beta$- or $\gamma$-interferon, antichemotactic factors, proteases specific for bacterial cell wall proteins, etc.

In addition to providing for expression of a gene having therapeutic value, there will be many situations where one may wish to direct a cell to a particular site. The site can include anatomical sites, such as lymph nodes, mucosal tissue, skin, synovium, lung or other internal organs or functional sites, such as clots, injured sites, sites of surgical manipulation, inflammation, infection, etc. By providing for expression of surface membrane proteins which will direct the host cell to the particular site by providing for binding at the host target site to a naturally-occurring epitope, localized concentrations of a secreted product can be achieved. Proteins of interest include homing receptors, e.g. L-selectin, GMP140, CLAM-1, etc., or addressing, e.g. ELAM-1, PNAd, LNAd, etc., clot binding proteins, or cell surface proteins that respond to localized gradients of chemotactic factors. There are numerous situations where one would wish to direct cells to a particular site, where release of a therapeutic product could be of great value.

For use in gene therapy, the target gene can encode any gene product that is beneficial to a subject. The gene product can be a secreted protein, a membraneous protein, or a cytoplasmic protein. Preferred secreted proteins include growth factors, differentiation factors, cytokines, interleukins, tPA, and erythropoietin. Preferred membraneous proteins include receptors, e.g, growth factor or cytokine receptors or proteins mediating apoptosis, e.g., Fas receptor. Other candidate therapeutic genes are disclosed in PCT/US93/01617.

In yet another embodiment, a "gene activation" construct which, by homologous recombination with a genomic DNA, alters the transcriptional regulatory sequences of an endogenous gene, can be used to introduce recognition elements for a DNA binding activity of one of the subject engineered proteins. A variety of different formats for the gene activation constructs are available. See, for example, the Transkaryotic Therapies, Inc PCT publications WO93/09222, WO95/31560, WO96/294 11, WO95/31560 and WO94/12650.

V. Methods of the Invention

The invention provides methods for stimulating transcription of a target gene, in particular, an integrated gene. The gene can be an endogenous gene, an exogenous gene, or a combination of both. The method of the invention comprises introducing into a target cell a multiplicity of transcriptional activation units linked to a DNA binding domain and/or a ligand binding domain. If the transcriptional activation units are linked to a ligand binding domain, then the method further comprises introducing into the cell a DNA binding domain linked to at least one ligand binding domain and a ligand capable of interacting with the ligand binding domains, such that the transcriptional activation units and DNA binding domain are interacting, thereby stimulating transcription of a target gene.

In another embodiment, the method of the invention comprises introducing into a target cell a multiplicity of ligand binding domains linked to a DNA binding domain together with at least one transcriptional activity unit linked to a ligand binding domain and a ligand which is capable of simultaneously binding to the two ligand binding domains. Thus, exposure of a target cell with an appropriate ligand will result in formation of a transcriptional activator complex comprising a multiplicity of activation units. Furthermore, since, as shown herein, the level of transcription of a target gene is directly correlated to the number of activation units that can be delivered to the target gene, the level of transcription of a target gene can be controlled by the level of ligand used to treat the target cell.

In a preferred embodiment, the method of the invention comprises introducing into a cell a target gene, a nucleic acid encoding a polypeptide having a multiplicity of activation units and a DNA binding domain or a ligand binding domain. If the polypeptide comprises a ligand binding domain, then the method further comprises introducing into the cell a nucleic acid encoding a polypeptide comprising a DNA binding domain and a ligand binding domain. The nucleic acids and vectors comprising such can be prepared as described above. These can be introduced into a cell comprising a target gene, i.e., target cell, according to methods known in the art. In embodiments in which the target cell is in vitro, the nucleic acids can be introduced into the target cell by transfection involving electroporation, chemical transformation (e.g., calcium chloride), liposomes, or viral transformation. In embodiments in which the target cell is in vivo, the nucleic acids can be introduced into the cell by direct injection of naked DNA, liposomes, or any other method of administration of nucleic acids to a subject.

VI Kits

This invention further provides kits useful for the foregoing applications. One such kit contains one or more nucleic acids encoding a transcriptional activator or subunits thereof. The kit may further comprise an additional nucleic acid containing a target gene linked to a DNA sequence to which the transcriptional activator is capable of binding. Alternatively, the additional nucleic acid may contain a cloning site for insertion of a desired target gene by the practitioner. For regulatable applications, i.e., in cases in which the recombinant protein contains a ligand binding domain or inducible domain, the kit may further contain an oligomerizing agent, such as the macrolide dimerizers discussed above. Such kits may for example contain a sample of a dimerizing agent capable of dimerizing the two recombinant proteins and activating transcription of the target gene.

VII. Exemplary Uses

The invention provides methods for stimulating transcription of a target gene at high levels, in particular of target genes integrated into chromosomal DNA. Strong transcriptional activators had not been prepared in the past, since it was known that potent transcriptional activators would induce squelching. However, as shown herein, transcription of an integrated gene can be stimulated at significantly higher levels than non-integrated genes due to the absence of squelching on integrated genes. This observation is important in the context of certain gene therapy applications because it suggests that highly potent transcriptional activators can be used to drive therapeutic gene expression to very high levels without general toxicity to the cell and that efficacious levels of secreted therapeutic proteins may be attained with fewer engineered cells than previously thought. Furthermore, the invention provides a method for controlling the level of transcription, by controlling the amount of transcriptional activation units delivered to the target gene by use of varying amounts of the oligomerizer.

In one embodiment, the invention is used to produce higher levels of a desired protein ex vivo. Production of recombinant therapeutic proteins for commercial and investigational purposes is often achieved through the use of mammalian cell lines engineered to express the protein at high level. The use of mammalian cells, rather than bacteria or yeast, is indicated where the proper function of the protein requires post-translational modifications not generally performed by heterologous cells. Examples of proteins produced commercially this way include erythropoietin, tissue plasminogen activator, clotting factors such as Factor VIII:c, antibodies, etc. The cost of producing proteins in this fashion is directly related to the level of expression achieved in the engineered cells. Thus, because the invention described herein can achieve considerably higher expression levels than conventional expression systems, it may greatly reduce the cost of protein production. A second limitation on the production of such proteins is toxicity to the host cell: Protein expression may prevent cells from growing to high density, sharply reducing production levels. Therefore, the ability to tightly control protein expression, as described for regulated gene therapy, permits cells to be grown to high density in the absence of protein production. Only after an optimum cell density is reached, is expression of the gene activated and the protein product subsequently harvested.

A similar problem is encountered in the construction and use of "packaging lines" for the production of recombinant viruses for commercial (e.g., gene therapy) and experimental use. These cell lines are engineered to produce viral proteins required for the assembly of infectious viral particles harboring defective recombinant genomes. Viral vectors that are dependent on such packaging lines include retrovirus, adenovirus, and adeno-associated virus. In the latter case, the titer of the virus stock obtained from a packaging line is directly related to the level of production of the viral rep and core proteins. But these proteins are highly toxic to the host cells. Therefore, it has proven difficult to generate high-titer recombinant viruses. This invention provides a solution to this problem, by allowing the construction of packaging lines in which the rep and core genes are placed under the control of regulatable transcription factors of the design described here. The packaging cell line can be grown to high density, infected with helper virus, and transfected with the recombinant viral genome. Then, expression of the viral proteins encoded by the packaging cells is induced by the addition of dimerizing agent to allow the production of virus at high titer.

In other embodiments, the subject constructs are used as part of a therapeutic treatment program from an animal. In one embodiment, the constructs of the invention are used to stimulate transcription of an endogenous gene of a subject. The endogenous gene can be any gene of the genome, increased expression of which is beneficial to a subject. For example, a subject may not produce sufficient amounts of a specific protein, due to a defect in a protein regulating the expression of the gene encoding the protein. In other embodiments, expression of a target gene is desired to compensate for the deficiency of expression of another gene. In yet other embodiments, the method of the invention is used to stimulate expression of an endogenous gene to compensate for a loss of the protein encoded by the endogenous gene. For example, the number of cells producing a specific secreted protein may be reduced in a subject, e.g, as the result of a disease or condition, thus resulting in reduced production of the specific factor in the subject.

In a preferred embodiment, the method of the invention is used to stimulate production of a factor which is necessary for the proliferation and/or differentiation of one or more specific cell types. For example, it may be desirable to stimulate the expression of growth factors and lymphokines in a subject in which at least some of the blood cells have been destroyed, e.g., by radiotherapy or chemotherapy. Accordingly, in a preferred embodiment, expression of the erythropoietin gene is stimulated in a subject, such that higher levels of erythropoietin are produced in the subject and that production of red blood cells is stimulated. Similarly in diseases or conditions in which one or more specific cell types are destroyed by the disease process, e.g., in autoimmune diseases, the specific cells can be replenished by stimulating expression of one or more genes encoding factors stimulating proliferation of these cells. The method of the invention can also be used to increase the number of lymphocytes in a subject having AIDS, such as by stimulating expression of lymphokines, e.g., IL-4, which stimulates proliferation of certain T helper (Th) cells.

At least one advantage of increasing the production of a specific protein in a subject by stimulating expression of the endogenous gene encoding the protein is the absence of an immune reaction against the protein, thus resulting in a more efficient treatment of the subject. Furthermore, for the same reason, it is desirable that the transcriptional activator or nucleic acid encoding such administered to a subject originate from the same species as that of the subject to which it is administered. In particular, it is preferable to administer a transcriptional activator of human origin to a human subject. However, transcriptional activators having activation tags which are not of human origin can also be used according to the methods of the invention. In such conditions, it may be preferable to simultaneously administer to the subject an immunosuppressant drug, e.g., cyclosporin A, or other compound which represses immune reactions. Immunosuppressive drugs are well known in the art.

Cells which have been modified ex vivo with the DNA constructs of the present invention may be grown in culture under selective conditions and cells which are selected as having the desired construct(s) may then be expanded and further analyzed, using, for example, the polymerase chain reaction for determining the presence of the construct in the host cells and/or assays for the production of the desired gene product(s). Once modified host cells have been identified, they may then be used as planned, e.g. grown in culture or introduced into a host organism.

Depending upon the nature of the cells, the cells may be introduced into a host organism, e.g. a mammal, in a wide variety of ways. Hematopoietic cells may be administered by injection into the vascular system, there being usually at least about $10^4$ cells and generally not more than about $10^{10}$ cells. The number of cells which are employed will depend upon a number of circumstances, the purpose for the introduction, the lifetime of the cells, the protocol to be used, for example, the number of administrations, the ability of the cells to multiply, the stability of the therapeutic agent, the physiologic need for the therapeutic agent, and the like. Generally, for myoblasts or fibroblasts for example, the number of cells will be at least about $10^4$ and not more than about $10^9$ and may be applied as a dispersion, generally being injected at or near the site of interest. The cells will usually be in a physiologically-acceptable medium.

Cells engineered in accordance with this invention may also be encapsulated, e.g. using conventional biocompatible materials and methods, prior to implantation into the host organism or patient for the production of a therapeutic protein. See e.g. Hguyen et al, Tissue Implant Systems and Methods for Sustaining viable High Cell Densities within a host, U.S. Pat. No. 5,314,471 (Baxter International, Inc.); Uludag and Sefton, 1993, J Biomed. Mater. Res. 27(10):1213–24 (HepG2 cells/hydroxyethyl methacrylate-methyl methacrylate membranes); Chang et al, 1993, Hum Gene Ther 4(4):433–40 (mouse Ltk-cells expressing hGH/ immunoprotective perm-selective alginate microcapsules; Reddy et al, 1993, J Infect Dis 168(4):1082–3 (alginate); Tai and Sun, 1993, FASEB J 7(11):1061–9 (mouse fibroblasts expressing hGH/alginate-poly-L-lysine-alginate membrane); Ao et al, 1995, Transplanataion Proc. 27(6):3349, 3350 (alginate); Rajotte et al, 1995, Transplantation Proc. 27(6):3389 (alginate); Lakey et al, 1995, Transplantation Proc. 27(6):3266 (alginate); Korbutt et al, 1995, Transplantation Proc. 27(6):3212 (alginate); Dorian et al, U.S. Pat. No. 5,429,821 (alginate); Emerich et al, 1993, Exp Neurol 122(l):37–47 (polymer-encapsulated PC12 cells); Sagen et al, 1993, J Neurosci 13(6):2415–23 (bovine chromaffin cells encapsulated in semipermeable polymer membrane and implanted into rat spinal subarachnoid space); Aebischer et al, 1994, Exp Neurol 126(2):151–8 (polymer-encapsulated rat PC12 cells implanted into monkeys; see also Aebischer, WO 92/19595); Savelkoul et al, 1994, J Immunol Methods 170(2):185–96 (encapsulated hybridomas producing antibodies; encapsulated transfected cell lines expressing various cytokines); Winn et al, 1994, PNAS USA 91(6):2324-8 (engineered BHK cells expressing human nerve growth factor encapsulated in an immunoisolation polymeric device and transplanted into rats); Emerich et al, 1994, Prog Neuropsychopharmacol Biol Psychiatry 18(5):935-46 (polymer-encapsulated PCI2 cells implanted into rats); Kordower et al, 1994, PNAS USA 91(23):10898–902 (polymer-encapsulated engineered BHK cells expressing hNGF implanted into monkeys) and Butler et al WO 95/04521 (encapsulated device). The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments the cells to be encapsulated may express one or more chimeric proteins containing component domains derived from proteins of the host species and/or from viral proteins or proteins from species other than the host species. For example in such cases the chimeras may contain elements derived from GAL4 and VP16. The cells may be derived from one or more individuals other than the recipient and may be derived from a species other than that of the recipient organism or patient.

Instead of ex vivo modification of the cells, in many situations one may wish to modify cells in vivo. For this purpose, various techniques have been developed for modification of target tissue and cells in vivo. A number of viral vectors have been developed, such as described above, which allow for transfection and, in some cases, integration of the virus into the host. See, for example, Dubensky et al. (1984) Proc. Natl. Acad. Sci. USA 81, 7529–7533; Kaneda et al., (1989) Science 243,375–378; Hiebert et al. (1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. The vector may be administered by injection, e.g. intravascularly or intramuscularly, inhalation, or other parenteral mode. Non-viral delivery methods such as administration of the DNA via complexes with liposomes or by injection, catheter or biolistics may also be used.

In accordance with in vivo genetic modification, the manner of the modification will depend on the nature of the tissue, the efficiency of cellular modification required, the number of opportunities to modify the particular cells, the accessibility of the tissue to the DNA composition to be introduced, and the like. By employing an attenuated or modified retrovirus carrying a target transcriptional initiation region, if desired, one can activate the virus using one of the subject transcription factor constructs, so that the virus may be produced and transfect adjacent cells.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

In another embodiment of the invention, the transcriptional activator of the invention recognizes a target endogenous gene, in which the promoter and/or one or more other regions of the gene has been modified to include a target sequence that is specifically recognized by the DNA binding domain of a known transcription factor and the transcriptional activator contains this DNA binding domain. Thus, the target endogenous gene is modified to be specifically recognized by a desired transcription factor. Such an embodiment can be useful in situations in which no DNA binding protein is known to specifically bind to a regulatory region of the target gene. Thus, in one embodiment, a cell is obtained from a subject and the cell is genetically engineered in vitro to insert a desired regulatory sequence into the promoter of the target gene. The cell can then be further administered to the subject. Alternatively, prior to administration of the cell to the subject, the cell can further be modified to include a nucleic acid encoding a transcriptional activator comprising a DNA binding domain which is capable of interacting specifically with the regulatory element introduced into the target gene. In another embodiment, an endogenous gene is modified in vivo by, e.g., homologous recombination.

Modification of a gene in a cell can be done, e.g., by homologous recombination, a technique well known in the art, and described, e.g., in Thomas and Capecchi (1987) Cell 51:503; Mansour et al. (1988) Nature 336:348; and Joyner et al. (1989) Nature 338:153.

In another embodiment, the transcriptional activator is used to stimulate transcription of an exogenous gene integrated into chromosomal DNA of a subject. An exogenous target gene can be introduced into a subject, by obtaining a cell from a subject, introducing the target gene and optionally a nucleic acid encoding a transcriptional activator into the cell and administering the cell to the subject. This embodiment is useful in situations in which in which no DNA binding protein is known to specifically bind to a regulatory region of the target gene or in situations in which the target gene encodes a protein which is not naturally produced by a cell. For example, the target gene can be a tumor antigen, which is not produced by the subject under normal conditions, but which one desires to express in the subject as a vaccine antigen to prevent development of a tumor expressing the tumor antigen.

Exogenous genes can also encode antisense RNA or ribozymes or other RNA molecules which are not translated. For example, the method of the invention can be used to inhibit production of one or more specific proteins in a cell of a subject. The availability of potent transcriptional activators provided by the invention will ensure that high levels of RNA, e.g., antisense RNA, are produced in a cell.

In a preferred embodiment of the invention, the transcriptional activator is a complex comprising a first fusion protein having multiple activation units and a ligand binding domain, a second fusion protein having a DNA binding domain and a ligand binding domain, and a ligand which interacts simultaneously with both ligand binding domains. Thus, activation of transcription of a target gene is stimulated only in the presence of the ligand, e.g., dimerizing agent. Accordingly, expression of the target gene in a subject is stimulated only upon administration of the ligand to the subject.

The dimerizing ligand may be administered to the patient as desired to activate transcription of the target gene. Depending upon the binding affinity of the ligand, the response desired, the manner of administration, the half-life, the number of cells present, various protocols may be employed. The ligand may be administered parenterally or orally. The number of administrations will depend upon the factors described above. The ligand may be taken orally as a pill, powder, or dispersion; bucally; sublingually; injected intravascularly, intraperitoneally, subcutaneously; by inhalation, or the like. The ligand (and monomeric antagonist compound) may be formulated using conventional methods and materials well known in the art for the various routes of administration. The precise dose and particular method of administration will depend upon the above factors and be determined by the attending physician or human or animal healthcare provider. For the most part, the manner of administration will be determined empirically.

In the event that transcriptional activation by the ligand is to be reversed or terminated, a monomeric compound which can compete with the dimerizing ligand may be administered. Thus, in the case of an adverse reaction or the desire to terminate the therapeutic effect, an antagonist to the dimerizing agent can be administered in any convenient way, particularly intravascularly, if a rapid reversal is desired. Alternatively, one may provide for the presence of an inactivation domain (or transcriptional silencer) with a DNA binding domain. In another approach, cells may be eliminated through apoptosis via signaling through Fas or TNF receptor as described elsewhere. See International Patent Applications PCT/US94/01617 and PCT/US94/08008.

The particular dosage of the ligand for any application may be determined in accordance with the procedures used for therapeutic dosage monitoring, where maintenance of a particular level of expression is desired over an extended period of times, for example, greater than about two weeks, or where there is repetitive therapy, with individual or repeated doses of ligand over short periods of time, with extended intervals, for example, two weeks or more. A dose of the ligand within a predetermined range would be given and monitored for response, so as to obtain a time-expression level relationship, as well as observing therapeutic response. Depending on the levels observed during the time period and the therapeutic response, one could provide a larger or smaller dose the next time, following the response. This process would be iteratively repeated until one obtained a dosage within the therapeutic range. Where the ligand is chronically administered, once the maintenance dosage of the ligand is determined, one could then do assays at extended intervals to be assured that the cellular system is providing the appropriate response and level of the expression product.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, it is expected that for each individual patient, even if there were universal cells which could be administered to the population at large, each patient would be monitored for the proper dosage for the individual.

In one embodiment of the invention, methods of introduction of an ligand, e.g., dimerizing agent, and/or a cell modified according to the method of the invention to synthesize high levels of protein from a target gene may be provided by rechargable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a dimerizer or a protein produced by a cell modified according to the method of the invention at a particular target site. Such embodiments of the present invention can be used for the delivery of an exogenously purified protein produced according to the method of the invention, which has been incorporated in the polymeric device, or for the delivery of a protein produced by a cell encapsulated in the polymeric device.

An essential feature of certain embodiments of the implant can be the linear release of the dimerizer or protein produced by the encapsulated cell which can be achieved through the manipulation of the polymer composition and form. By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, Concise Encylopedia of Medical & Dental Materials, ed. by David Williams (MIT Press: Cambridge, Mass., 1990); and the Sabel et al. U.S. Pat. No. 4,883,666. In another embodiment of an implant, a source of cells, modified according to the method of the invention, producing a desired protein, or a solution of hydogel matrix containing purifed protein or dimerizer, is encapsulated in implantable hollow fibers. Such fibers can be pre-spun and subsequently loaded with the protein source or dimerizer (Aebischer et al. U.S. Pat. No. 4,892,538; Aebischer et al. U.S. Pat. No. 5,106,627; Hoffman et al. (1990) Expt. Neurobiol. 110:39–44; Jaeger et al. (1990) Prog. Brain Res. 82:41–46; and Aebischer et al. (1991) J. Biomech. Eng. 113:178–183), or can be co-extruded with a polymer which acts to form a polymeric coat about the cell, protein or dimerizer (Lim U.S. Pat. No. 4,391,909; Sefton U.S. Pat. No. 4,353,888; Sugamori et al. (1989) Trans. Am. Artif. Intern. Organs 35:791–799; Sefton et al. (1987) Biotehnol. Bioeng. 29:1135–1143; and Aebischer et al. (1991) Biomaterials 12:50–55).

Thus, the method of the invention can broadly be applied to any situation, e.g., for treating or preventing any disease or condition, in which transcriptional activation of an integrated target gene is desired. Depending on the specific embodiment of the invention, a transcriptional activator, nucleic acid encoding such, target exogenous gene, and/or oligomerizer is administered to a subject. These an be administered as such or together with a delivery vehicle, e.g., liposomes. Whether with or without a delivery vehicle, these compounds are preferably administered together with a pharmaceutically acceptable carrier. Methods of administration of these compounds are known in the art and are briefly disclosed below.

Toxicity and therapeutic efficacy of such compounds can be determined by standard pharmaceutical procedures in cell cultures or experimental animals, e.g., for determining the $Ld_{50}$ (the dose lethal to 50% of the population) and the $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e. g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

In clinical settings, the gene delivery systems for the genes encoding transcriptional activators and optionally target gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91:3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The present invention is further illustrated by the following examples which should not be construed as limiting in any way. The contents of all cited references including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning†A Laboratory†Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

Exemplification

The invention now being generally described, it will be more readily understood by reference to the following examples which are included merely for purposes of illustration of certain aspects and embodiments of the present invention, and are not intended to limit the invention.

EXAMPLE 1:

Stimulation of High Level Transcription of an Integrated Gene

This Example shows that a gene integrated into chromosomal DNA is immune from the effect of squelching and that high level transcription of an integrated gene can be obtained by delivering multiple activation domains to the gene.

First, the effect of increasing concentrations of a transcriptional activator on an integrated versus a non-integrated reporter gene was compared as follows. Two constructs encoding chimeric transcriptional activators under the control of the CMV enhancer/promoter were used. The first construct (pCG-GV) encodes a chimeric transcription factor composed of the yeast GAL4 DNA-binding domain (amino acids 1–94) and activation domain (amino acids 410–490) derived from the herpes simplex virus protein VP16 (Sadowski, I., et al. (1988) Nature 335:563–4). The second construct (pCG-CS) encodes a chimeric transcription factor composed of the yeast GAL4 DNA-binding domain (amino acids 1–94) and the activation domain (amino acids 361–550) from the NF-B p65 protein (Ballard, D. W., et al. (1991) Proc. Natl. Acad. Sci 89:1875–1879; Schmitz, M. L. and Baeuerle, P. A. (1991) EMBO J. 10:3805–3817). The effect of these transcription factors was tested on a target gene composed of a secreted alkaline phosphatase (SEAP) reporter under the control of a minimal human IL-2 gene promoter flanked by five GAL4 binding sites.

HT1080 cells were transiently transfected with the reporter construct and/or a construct encoding a chimeric transcription factor as follows. HT1080 cells were grown at 37° C. in MEM medium containing 10% fetal calf serum, non-essential amino acids and penicillin-streptomycin. Twenty-four hours before transfection, approximately $2 \times 10^5$ cells were seeded in each well in a 12-well plate. Cells were transfected using Lipofectamine as recommended (Gibco BRL). Cells in each well received the amount of plasmids indicated in the figure, with or without 400 ng of reporter plasmid, with the total amount of DNA being adjusted to 1.25 µg with pUC 19. Five hours later, the medium was removed and 1 ml of fresh medium added. 18–24 hours later, 100 µl medium was removed and assayed for SEAP activity using a Luminescence Spectrometer (Perkin Elmer) at 350 nm excitation and 450 nm emission.

HT1080 cells were stably transfected with the reporter construct pLH-5xGAL4-IL2-SEAP as follows. The retroviral vector pLH-5xGal4-IL2-SEAP was constructed by cloning the 5xGAL4- IL2-SEAP fragment described above into the vector pLH (Rivera, V. M., et al. (1996) Nature Medicine 2:1028–1032), which also contains the hygromycin B resistance gene driven by the Moloney murine leukemia virus long terminal repeat. Helper-free retrovirus, generated as described (Rivera, V. M., et al. Nature Medicine 2,1028–1032 (1996)) was used to infect HT1080 cells. Hundreds of hygromycin B (300 µg/ml) resistant clones were pooled (HT1080 B pool) and individual clones screened by transient transfection with pCG-GS. The most responsive clone, HT1080B, was selected for further analysis.

Figure 1B:
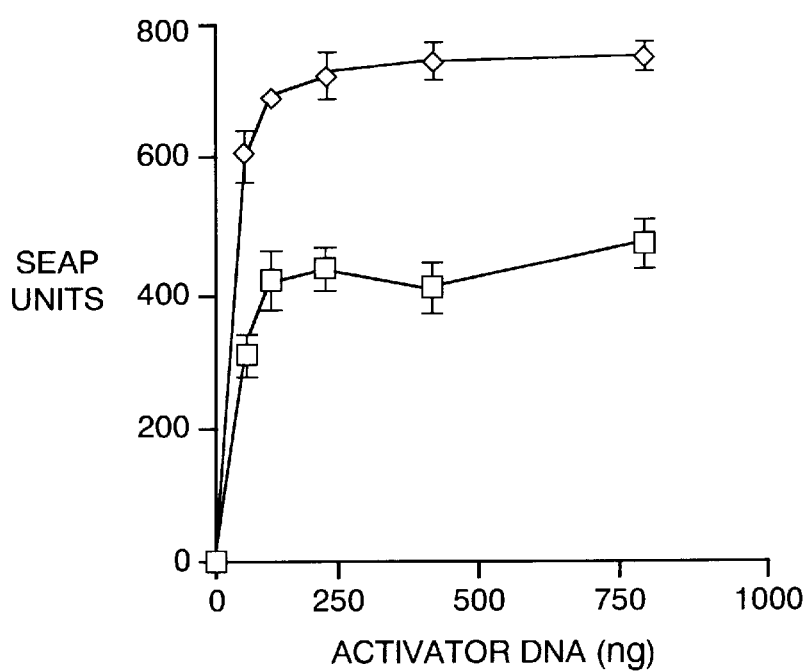
FIG. 1B shows the level of reporter gene expression (in EAP Units) from a clone of HT1080 cells (HT1080B) having an integrated plasmid cotransfected with various amounts of GAL,4-p65 (diamonds) or GAL4-VP 16 (squares) expression constructs. Mean values of SEAP activity secreted into the medium are shown (+/–S.D.).

When the reporter gene and expression plasmids encoding the transcription factors were both introduced transiently into HT1080 human fibrosarcoma cells, peak reporter gene expression at relatively low levels of input activator plasmid was observed, while higher levels of activator led to a sharp reduction in reporter gene expression (FIG. 1A). This inhibition of gene expression in the presence of high levels of activator has been widely observed, and the phenomenon has been termed "squelching." On the contrary, expression of the integrated reporter gene was not inhibited by levels of activator that sharply squelched a transiently transfected reporter (FIG. 1B).

Figure 1C:
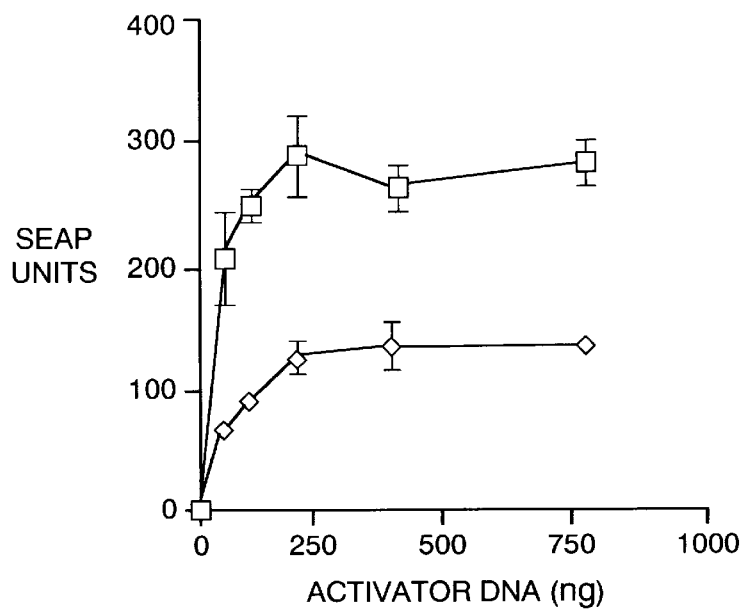
FIG. 1C shows the level of reporter gene expression (in EAP Units) in a pool of hundreds of independent IIT1080 clones carrying an integrated plasmid pLH-5xGAL4-IL2-SEAP cotransfected with various amounts of GAL4-p65 (diamonds) or GAL4-VP16 (squares) expression constructs. Mean values of SEAP activity secreted into the medium are shown (+/–S.D.).

To rule out the possibility that the immunity of the integrated gene to squelching reflects the effect of a single unusual integration site, this experiment was repeated using a pool of several hundred HT1080-derived clones harboring independent reporter gene insertions. As shown in FIG. 1C, expression of this population of inserted reporter genes was not inhibited by high levels of activator. A second reporter construct in which the same GAL4-driven IL-2 promoter was fused to a human growth hormone (hGH) reporter gene was constructed by replacing the SEAP gene with the hGH gene. This plasmid was cotransfected with the GAL4-p65 expression plasmid into cells containing an integrated SEAP reporter gene, thus allowing both reporter genes to be assayed in the same cell population. Transfections and reporter gene expression were measured as described above. For determining expression of the hGH reporter construct, 2–5 μl of medium was assayed for hGH protein as recommended (Nichols Diagnostic).

Figure 2:
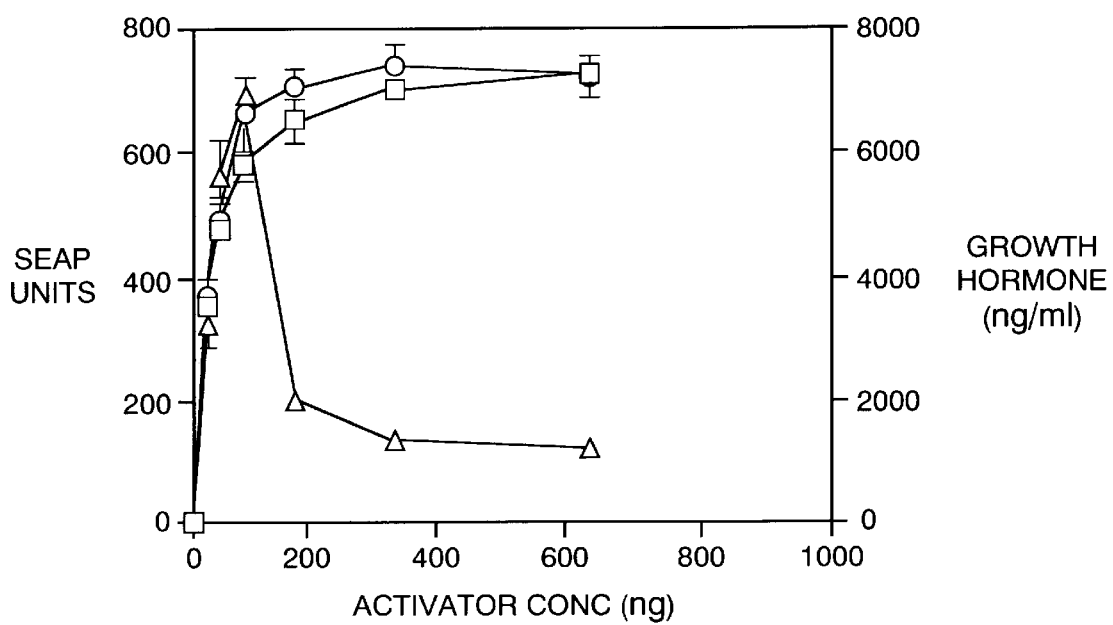
FIG. 2 shows the transcriptional activity of the integrated SEAP gene from pLH-5xGAL4-IL2SEAP plasmid in the presence (squares) or absence (circles) of cotransfected 5xGAL4-IL2-hGH reporter plasmid, as well as the transcriptional activity of the transiently transfected 5xGAL4-IL2-hGH reporter plasmid (triangles) in HT1080 cells cotransfected with various amounts of GAL1-p65 expression construct (Activator). Mean values of SEAP activity and hGH protein secreted into the medium are shown (+/–S.D.).

If in the presence of a high-copy episomal template, GAL4-p65 titrates GTFs necessary for the activity of this promoter, then one would expect to observe inhibition of both the episomal hGH gene and the integrated SEAP gene. However, the results indicate that, whereas expression of the episomal hGH gene was inhibited at high activator concentrations, the integrated SEAP gene responded identically whether or not the episomal gene was present (FIG. 2). Similar results were obtained in parallel experiments with GAL4-VP16. This observation indicates that one or more mechanistic steps in the transcription cycle differ between episomal and integrated genes.

EXAMPLE 2

Transcription of an Integrated Gene Increases Proportionally to the Number of Activation Domains Delivered to the Gene This Example shows that expression of an integrated gene can be driven to very high levels by delivering many potent activation domains to the promoter of the gene.

A modular strategy was designed to deliver different numbers of activation domains to a single integrated target gene. This strategy was based on the ability of a small-molecule "dimerizer" to recruit activation domains to a DNA-bound receptor (Belshaw, P. J., et al. (1996) Proc. Natl. Acad. Sci 93:4604–4607; Rivera, V. M., et al. (1996) Nature Medicine 2:1028–1032; Ho, S. N., et al. (1996) Nature 382:822–824). The basic system, which is diagrammed in FIG. 3A, was composed of a GAL4 DNA-binding domain fused to a single copy of human FKBP12 and a p65 activation domain fused to the FRB domain of FRAP (Ho, S. N., et al., supra; Sabatini, D. M., et al. (1994) Cell 78:35–43). In the presence of the natural-product immunosuppressive compound rapamycin, the FRB-p65 fusion protein is efficiently recruited to the GAL4-FKBP fusion protein. This basic system results in the delivery of a maximum of one p65 activation domain per GAL4 monomer. The number of deliverable activation domains was increased in two ways: (i) by increasing the number of FKBP moieties fused to GAL4, as indicated in FIG. 3B; and (ii) through the use of a tetramerization domain derived from the E. coli lac repressor (Chakerian, A. E., et al. (1991) J Biol Chem 266:1371–4; Alberta, S., et al. (1993) EMBO J. 12:3227–36; Lewis, M., et al. (1996) Nature 271:1247–1254) to deliver "bundles" of four activation domains to each FKBP moiety, as shown in FIG. 3C. These different configurations allowed recruitment of up to sixteen p65 activation domains to a single GAL4 monomer.

These expression constructs were prepared as follows. pCGNN-G expression vector was made by inserting a PCR fragment containing the GAL4 DNA binding domain (amino acids 1–94) flanked by upstream XbaI and downstream SpeI and BamHI sites into XbaI- and BamHI- digested pCGNN. FKBP12 coding sequence (amino acids 1–107), flanked by upstream XbaI and downstream SpeI and BamHI sites was inserted between the SpeI and BamHI sites of pCGNN-G to generate pCGNN-GF1. Plasmids pCGNN-GF2, GF3 and GF4 were made by the sequential insertion of FKBP12 coding sequences into SpeI- and BamHI digested pCGNN-GF1, 2 and 3 plasmids, respectively. PCGNN-RL was constructed by cloning an XbaI-BamHI fragment containing a portion of the E. coli lactose repressor (amino acids 46–360) into SpeI- and BamHI-digested pCGNN-R (Rivera, V. M., et al. supra) to fuse it to the carboxy terminus of the FRB domain. The p65 activation domain was fused to the carboxy terminus of this chimera by inserting an XbaI-BamHI fragment into SpeI- and BamHI digested pCGNN-RL to create pCGNN-RLS.

Figure 4A:
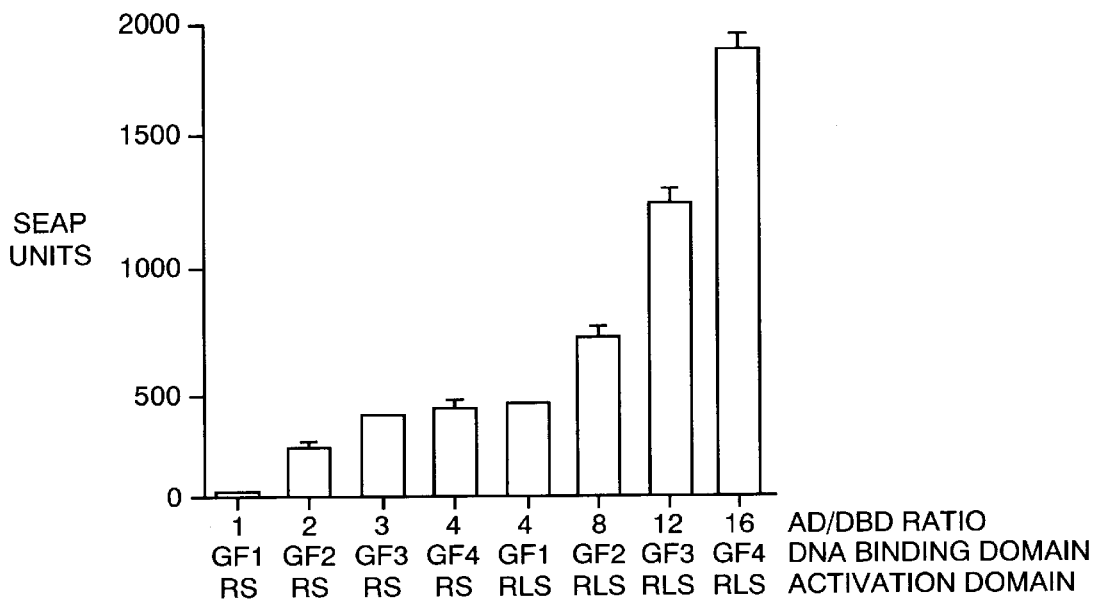
FIG. 4A represents the level of reporter gene expression (SEAP Units) of a stably integrated pLH-5xGAL,4-IL2-SEAP plasmid in HT1080B cells cotransfected with a plasmid encoding a GAL4DNA binding domain linked to 1, 2, 3, or 4 FKBP12 proteins (GF1, GF2, GF3, and GF4, respectively) and a either a plasmid encoding FRB fused to p65 activation domain (RS) or a plasmid encoding FRB fused to the E. coli tetramerization domain and p65 activation domain (RSL) in the presence of 10 nM rapamycin. Mean values of SEAP activity secreted into the medium following addition of 10 nM rapamycin are shown (+/–S.D.). AD/DBD ratio indicates the ratio between the amount of plasmid encoding an activation domain (AD) and a plasmid encoding a GAL4 DNA binding domain (DBD).
Figure 4B:
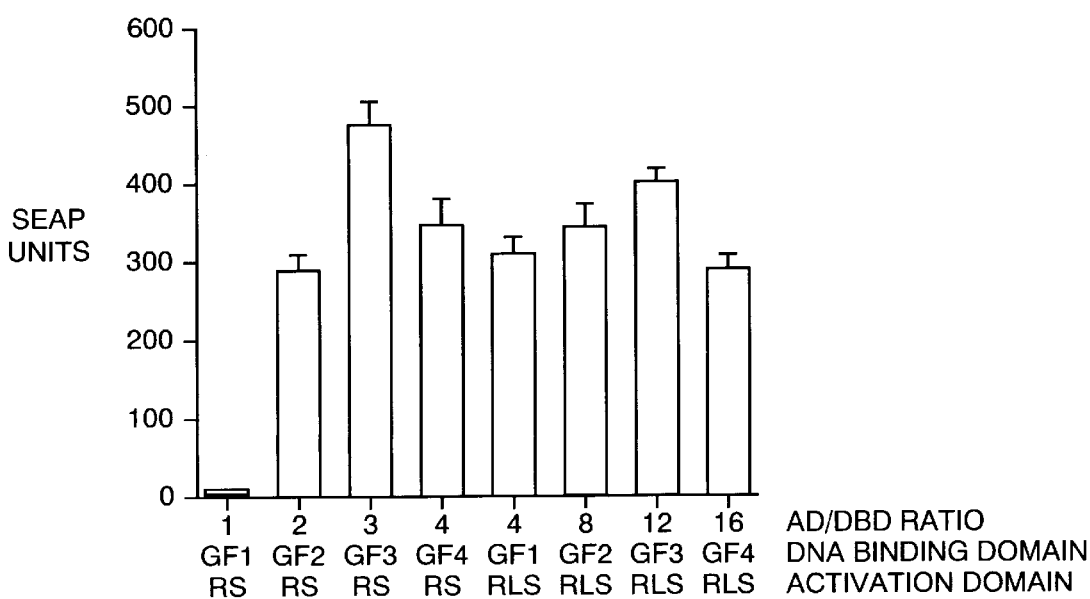
FIG. 4B represents the level of reporter gene expression (SEAP Units) of a transiently transfected 5xGAL4-IL2-SEAP plasmid in HT1080 cells cotransfected with a plasmid encoding a GAL4DNA binding domain linked to 1, 2, 3, or 4 FKBP12 proteins (GF1, GF2, GF3, and GF4, respectively) and a either a plasmid encoding FRB fused to p65 activation domain (RS) or a plasmid encoding FRB fused to the E. coli tetramerization domain and p65 activation domain (RSL) in the presence of 10 nM rapamycin. Mean values of SEAP activity secreted into the medium following addition of 10 nM rapamycin are shown (+/–S.D.). AD/DBD ratio indicates the ratio between the amount of plasmid encoding a encoding an activation domain (AD) and a plasmid encoding a GAL4 DNA binding domain (DBD).
Figure 5:
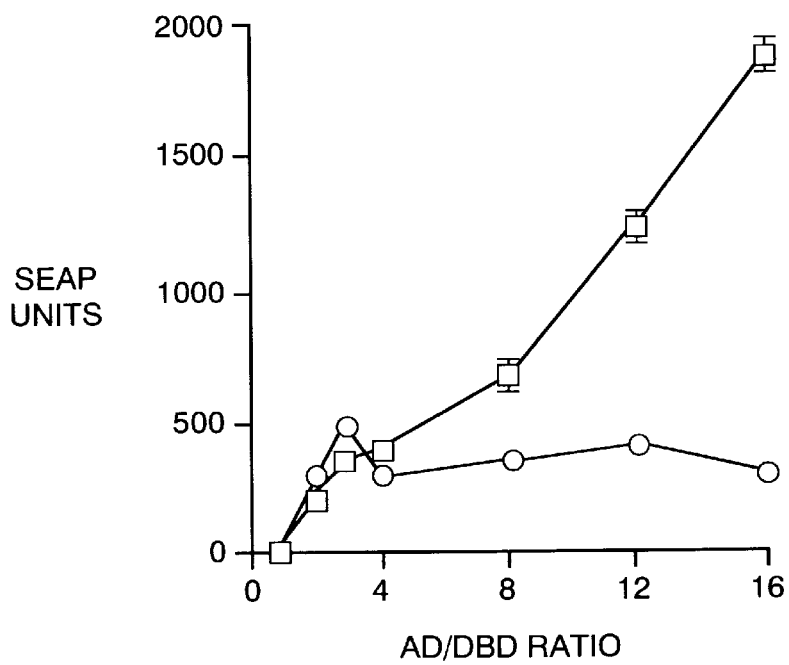
FIG. 5 shows the level of reporter gene expression (SEAP Units) of an integrated SEAP gene in HT1080B cells transiently transfected with varying amounts of GAL4-p65 plasmid in the absence (square) or presence of either 120 nM trichostatin A (diamond) 1 mM sodium butyrate (circle). Median values of SEAP activity secreted into the medium are shown (+/–S.D).

Various combinations of expression constructs, i.e., 10 ng of plasmid expressing DNA binding domain fusions and increasing amounts of plasmid expressing p65 activation domain fusions were transfected into HT1080B cells carrying an integrated reporter gene. The cells were then treated with 10 nM rapamycin to deliver the activation domains to the target gene and the amount of SEAP was measured in the supernatant. As shown in FIGS. 4A and 4B, the results indicate a roughly linear increase in reporter gene expression as a function of the number of activation domains that are delivered to a single GAL4 monomer. In contrast, except for the increment from one to two activation domains per GAL4 monomer, increasing the number of activation domains that can be delivered to an episomal target gene (introduced by transient transfection) failed to enhance the peak level of gene expression achieved before squelching occurred (FIGS. 4A and 4B).

These results indicate that expression of the episomal reporter gene can be driven only to a fixed level before squelching sets in, effectively establishing a ceiling for expression from the episomal gene. Because squelching does not impose such a limitation on the integrated gene, expression can be substantially augmented by delivering more activation domains, indicating that expression of an integrated chromatin-embedded gene is limited largely by the number (or strength) of activation domains bound at the promoter. Furthermore, the level of expression reached by the integrated gene is considerably higher than that attained by the episomal gene, especially when considered on a per-template basis, as shown in FIG. 4A.

EXAMPLE 3

Transcriptional Activation Units can Synergize to Activate Transcription of an Integrated Target Gene This Example shows that specific combinations of transcriptional activation domains can result in potent transcriptional activators capable of strong transactivation of integrated single copy genes.

The effect of various constructs encoding GAL4 DNA binding domain fusion proteins on transcription of an integrated pLH-5xGal4-IL2-SEAP vector in HT1080 cells (clone HT1080B) was determined. The activation domains fused to the GAL4 DNA binding domain (amino acids 1–94) consisted of amino acids 18×4 of QIII (GQIII), amino acids 1–92 of p53 (Gp53), amino acids 417–490 of VP16 (GVP16), amino acids 450–550 of p65 (Gp65), amino acids 399–499 of CTF (GCTF), amino acids 411–508 of SRF (GSRF), or amino acids 263–499 of SP1 (GSP1).

Figure 6:
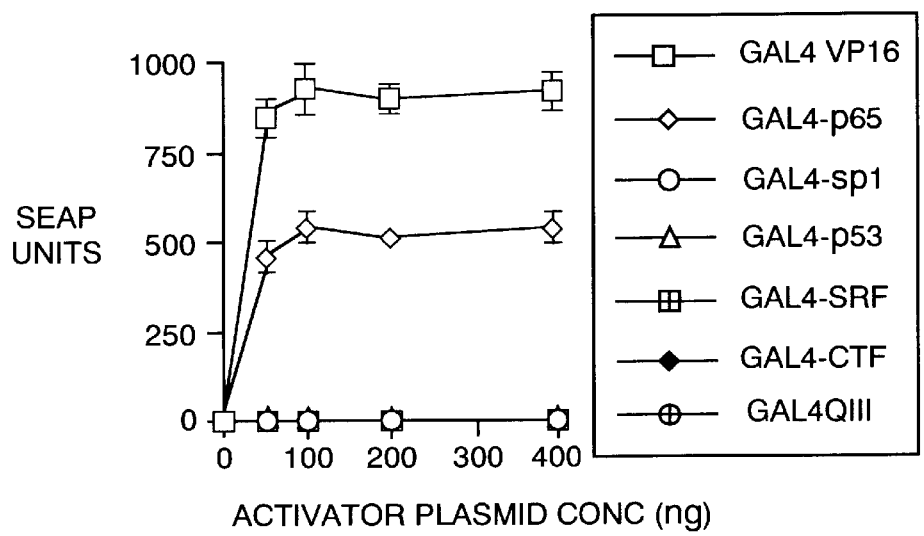
FIG. 6 shows the level of reporter gene expression (SEAP Units) of an integrated SEAP gene in HT1080B cells transiently transfected with expression vectors encoding GAL4 fusion proteins having an activation domain from various transcription factors.

Various amounts of these constructs were transiently transfected into the HT1080B cell line having a single integrated copy of the vector pLH-5xGal4-IL2-SEAP and the level of expression of the reporter gene was measured as described above. The results, which are represented in FIG. 6, indicate that among the various fusion proteins, only GAL4-VP16 and GAL4-p65 activate transcription of the integrated single copy reporter gene.

Figure 7:
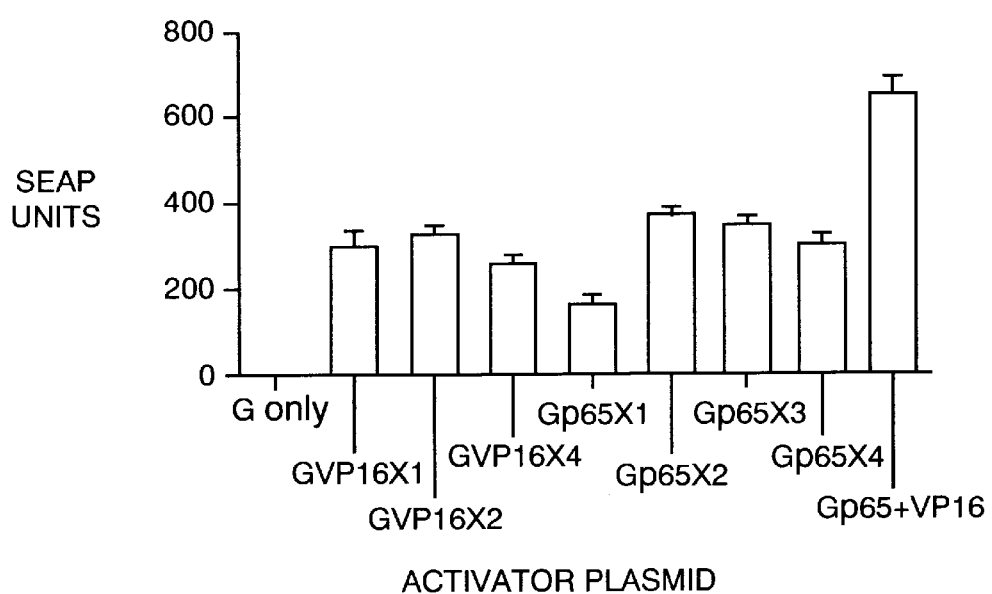
FIG. 7 shows the level of reporter gene expression (SEAP Units) of an integrated SEAP gene in HT1080B cells transiently transfected with expression vectors encoding GAL4 fusion proteins having no activation domain (G only); 1, 2, or 4 activation domains from VP16 (GVP16X1, GVP16X2, and GVP16X3, respectively); 1, 2, 3, or 4 activation domains from p65 (Gp65X1, Gp65X2, Gp65X3, and Gp65X4, respectively); or a combination of an activation domain from VP16 and an activation domain from p65 (Gp65+VP16).

Next, the transactivation potential of combinations of transcriptional activation domains were tested on a single copy integrated gene. Expression constructs encoding a GAL4 DNA binding domain linked to 1, 2, or 4 VP16 activation domains (amino acids 417–490) or 1, 2, 3, or 4 p65 activation domains (amino acids 450–550) or a p65 activation domain fused to a VP16 activation domain. The results are presented in FIG. 7 and indicate that a multiplicity of p65 activation domains or VP16 activation domains do not provide higher levels of transcription relative to a transcriptional activator containing a single p65 or VP16 activation domain. In contrast, the activation domains of p65 and VP16 are capable of cooperating in transcriptional activation of an integrated target gene.

Figure 8A:
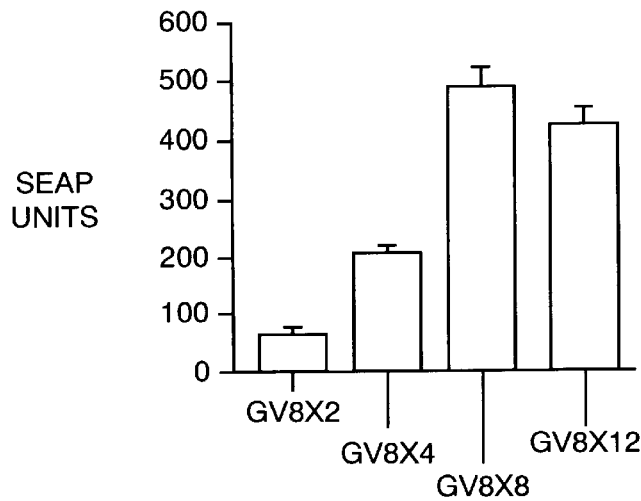
FIG. 8A shows the level of reporter gene expression (SEAP Units) of an integrated SEAP gene in HT1080B cells transiently transfected with expression vectors encoding GAL4 fusion proteins having 2, 4, 8, or 12 copies of the V8 (GV8X2, GV8X4, GV8X8, and GV8X12, respectively).
Figure 8B:
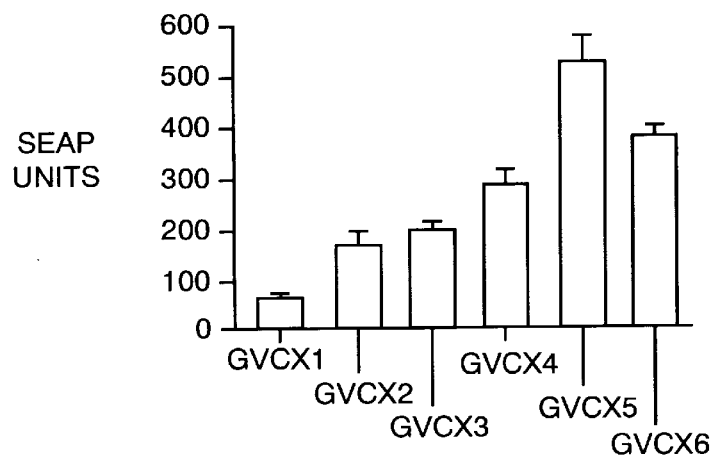
FIG. 8B shows the level of reporter gene expression (SEAP Units) of an integrated SEAP gene in HT1080B cells transiently transfected with expression vectors encoding GAL4 fusion proteins having 1, 2, 3, 4, 5, or 6 copies of the Vc (GVCX2, GVCX3, GVCX4, GVCX5, and GVCX6, respectively).
Figure 8C:
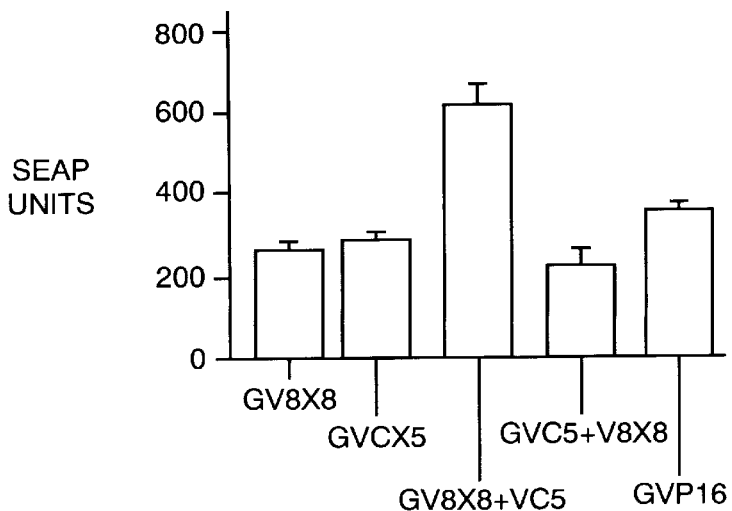
FIG. 8C shows the level of reporter gene expression (SEAP Units) of an integrated SEAP gene in HT1080B cells transiently transfected with expression vectors encoding GAL4 fusion proteins having 8 V8 copies (GV8X8), 5 Vc copies (GVCX5), 8 copies of V8 and 5 copies of Vc (GV8X8+GVCX5), 8 copies of V8 and 5 copies of Vc in the reverse order (GVCX5+GV8X8), or VP16 (GVP16).

In another experiment, the transcriptional potential of combinations of transcriptional activation domains of VP16 on a single copy integrated gene was determined. Expression constructs encoding the following fusion proteins containing a GAL4 DNA binding domain (amino acids 1–94) were prepared and tested in transient transfections of the HT1080 cell clone containing a single integrated vector pLH-5xGal4-IL2-SEAP: fusion proteins containing 2, 4, 8, or 12 copies (GV8X2, GV8X4, GV8X8, and GV8X12, respectively) of an eight amino acid variant of a transactivation domain from VP16 having the amino acid sequence (SEQ ID No:3) DFDLDMLG (referred to herein as "V8" peptide); fusion proteins containing 1, 2, 3, 4, 5, or 6 copies (GVCX1, GVCX2, GVCX3, GVCX4, GVCX5, GVCX6, respectively) of a transactivation domain from the C-terminus of VP16 corresponding to amino acids 461–490 (referred to herein as "Vc peptide); and fusion proteins containing 8 copies of V8 and 5 copies of Vc, wherein the V8 copies are fused either to the N-terminus or the C-terminus of Vc. The results, which are presented in FIG. 8, panels A and B, indicate cooperativity between V8 peptides up to about 8 copies of V8 and up to 5 copies of Vc. Higher numbers of copies of V8 and Vc result in reduced transcriptional activity of the reporter gene. However, as shown in FIG. 8, panel C, a combination of 8 copies of V8 fused to the N-terminus of 5 copies of Vc, results in stronger transcriptional levels than that obtained with either 8 copies of V8 or 5 copies of Vc. This transcriptional level is even higher than that obtained with full length VP16. Interestingly however, a fusion protein containing 8 copies of V8 fused to the C-terminus of 5 copies of Vc does not result in higher transcriptional activity of the reporter constructs, relative to 8 copies of V8 and 5 copies of Vc. Thus, specific arrangements of transcriptional activation domains are more potent in activating transcription than other arrangements.

Thus, this example demonstrates that combination of multiple activation domains can result in potent transcriptional activators capable of stimulating transcription of a single copy integrated gene.

EXAMPLE 4

An Alanine/Proline Rich Domain of p65 is Capable of Strongly Transactivating a Target Gene, when in the Presence of Another Transactivation Domain This Example demonstrates that a specific domain of gp65 is incapable to stimulate transcription of a target gene on its own, but can synergize with other transcriptional activation domains to stimulate transcription of a target gene.

Analysis of the p65 amino acid sequence revealed the presence of two Alanine/Proline rich regions in p65. The first domain, i.e., domain I, consists of amino acids 376–401 and has the amino acid sequence SALALAPAPPQVLPQA-PAPAPAPAMV (SEQ ID NO.10). The second domain, i.e., domain II, consists of amino acids 402–427 and has the amino acid sequence SALAQAPAPVPVLAPGPPQAVAP-PAP (SEQ ID NO.11). The transcriptional potential of these sequences was investigated as follows. Constructs encoding fusion proteins containing GAL4 DNA binding domain (amino acids 1–92) and the following domains were prepared for use in transient transfection: fusion proteins containing 1, 2, or 3 copies of amino acids 361–450 of p65 containing the two above-described alanine/proline rich regions and referred to herein as the AP domain; fusion proteins containing 1, 2, or 4 copies of the SP1 activation domain; and fusion proteins containing an SP1 activation domain fused at its N-terminal or C-terminal region to one or two AP domains.

Figure 9A:
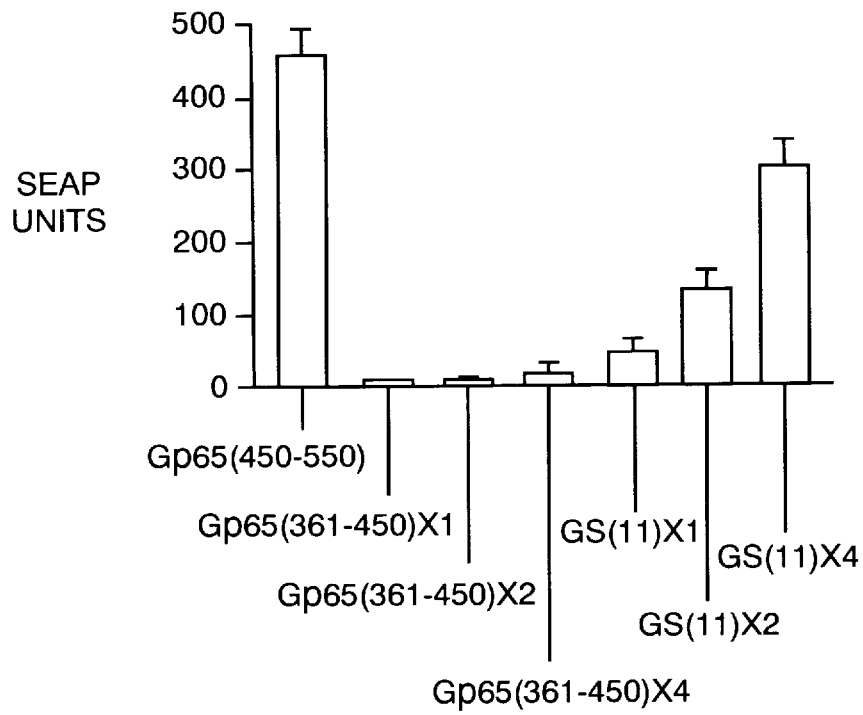
FIG. 9A shows the level of reporter gene expression (SEAP Units) of an integrated SEAP gene in HT1080B cells transiently transfected with expression vectors encoding GAL4 fusion proteins having amino acids 450–550 of p65 (Gp65 (450–550)); 1, 2, or 4 copies of amino acids 361–450 of p65; or 1, 2, or 4 copies of an activation domain from Sp1.
Figure 9B:
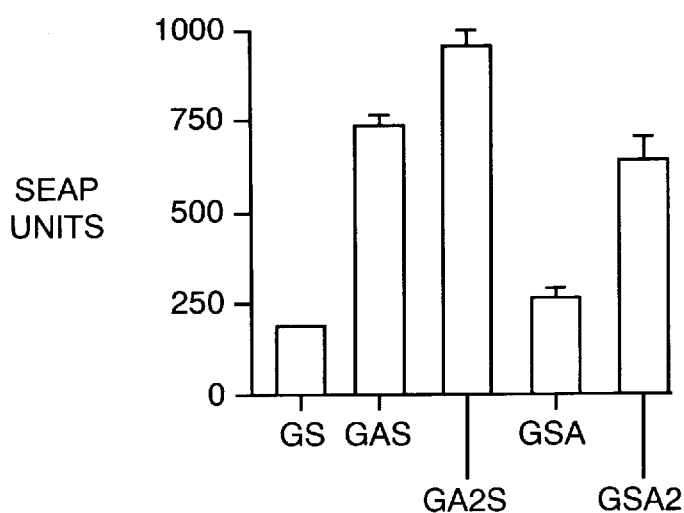
FIG. 9B shows the level of reporter gene expression (SEAP Units) of an integrated SEAP gene in HT1080B cells transiently transfected with expression vectors encoding GAL4 fusion proteins having an Sp1 activation domain alone (GS) or together with one or two copies of the AP domain.

The amount of reporter gene expression obtained upon transfection of these constructs into the HT1080B cell line containing an integrated copy of the vector pLH-5xGal4-IL2-SEAP is shown in FIGS. 9A and B. These results indicate that 2 and 4 copies of the AP domain does not result in significant transactivation of the reporter gene, in contrast to an increase in transcription proportional to the number of Sp1 domains added (FIG. 9A). However, the combination of one or more AP domains with an Sp1 activation domain synergistically activated transcription of the reporter construct (FIG. 9B). Interestingly, the synergy appears to be stronger when the AP domain is linked to the N-terminus of the Sp1 activation domain. Thus, a combination of transcriptional activation domains results in transcriptional activators which can be much more potent than naturally occurring transcription factors.

Figure 10A:
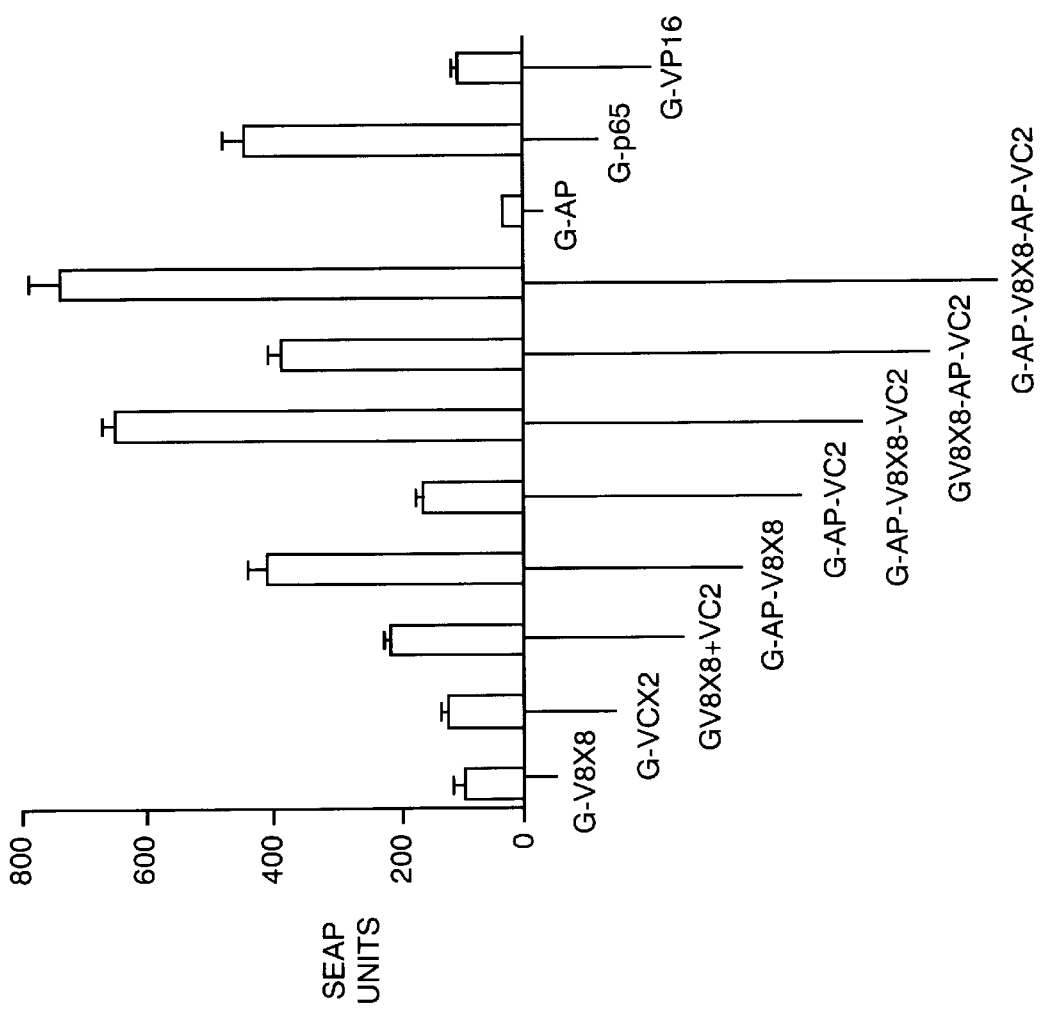
FIG. 10A shows the level of reporter gene expression (SEAP Units) of an integrated SEAP gene in HT1080B cells transiently transfected with expression vectors encoding GAL4 fusion proteins various activation domains or combinations thereof.
Figure 10B:
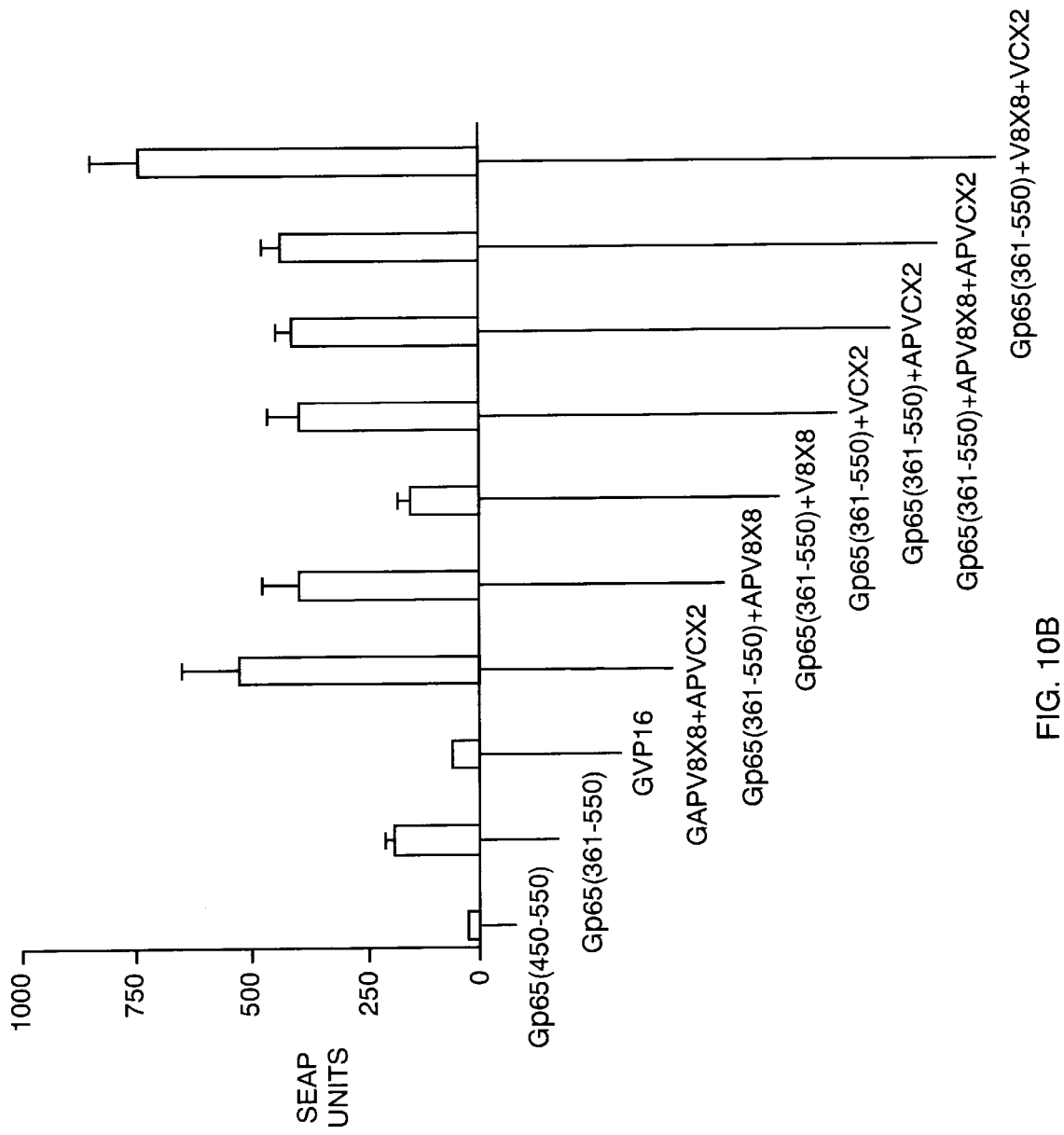
FIG. 10B shows the level of reporter gene expression (SEAP Units) of an integrated SEAP gene in HT1080B cells transiently transfected with expression vectors encoding GAL4 fusion proteins various activation domains or combinations thereof.

Yet other combinations of transactivation domains were tested for their effect on transcription of an integrated single copy gene. The fusion proteins tested comprised a GAL4 DNA binding domain and one or more V8 domains, one or more Vc domains, and/or one or more AP domains. Expression constructs encoding these fusion proteins were transiently transfected into the HT1080 cell line containing an integrated copy of the vector pLH-5xGal4-IL2-SEAP. The results are shown in FIGS. 10A and 10B. These results show that the AP domain potentiates the transcriptional activation of various combinations of transcriptional activation domains. However, the AP domain has a stronger potentiating effect on some activation domains than on others. In particular, as shown in FIG. 10A, AP synergizes with V8, but increases only slightly transcription by Vc. While not wishing to be bound by any particular theory, we note that one possible explanation for this phenomenon is that both the AP domain and Vc interact with the same GTF, i.e., TFIIA, whereas V8 interacts with a different GTF. Thus, it is possible that synergy between different transcriptional activation domains is induced when the activation domains interact with different GTFs. FIG. 10A further shows that certain combinations of activation domains, such as AP-V8x8-Vcx2 and AP-V8x8-AP-Vcx2, are capable of stimulating transcription of the reporter gene to higher levels than VP16 and even p65, which is one of the most potent naturally occurring transcription factors known.

FIG. 10B shows the results of transfections with yet other fusion proteins having various combination of transactivating domains. In particular, FIG. 10B shows that the transcriptional activity of a transcriptional activation domain of p65, corresponding to amino acids 361–550 (containing the AP domain) is further potentiated by the addition of one or more other transactivation domains, such as an additional AP domain and/or V8 or Vc domains.

In yet another set of transfections, constructs encoding fusion proteins having activation domains fused to three copies of the ligand binding domain FKBP, DNA binding domains fused to ligand binding domains (FKBP or FRB in a single or mutliple copies) were used. In these transfections, transcription was induced by addition of a ligand, e.g., rapamycin, FK1012, AP1510, or other synthetic dimerizer (depending on the ligand binding domain). The results obtained were similar to those obtained with the covalent system.

Thus, this Example shows that potent transcriptional activators can be created by the combination of various transcriptional activation domains and that these transcriptional activators stimulate transcription of an integrated single copy gene.

All of the above-cited references and publications are hereby incorporated by reference.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention.

I claim:

1. A nucleic acid encoding a chimeric transcription activator protein which
    (a) includes at least one composite transcription activation domain comprising three or more transcriptional activation tags which are mutually heterologous and do not occur in nature in the same gene product, wherein each transcriptional activation tag, alone or together with another transcriptional activation tag, activates transcription in a cell of a gene to which the chimeric transcription activator protein binds;
    (b) includes at least one additional domain comprising a DNA-binding domain; and (c) activates transcription of a gene to which the chimeric transcription activator protein binds.

2. A nucleic acid composition comprising a first nucleic acid encoding a chimeric transcription activator protein of claim 1 and a target gene construct comprising a target gene operatively linked to an expression control sequence which includes a DNA sequence to which the chimeric transcription activator protein binds.

3. A nucleic acid encoding a chimeric transcription activator protein which:
(a) includes at least one composite transcription activation domain comprising two or more transcriptional activation tags which are mutually heterologous, wherein each transcriptional activation tag, alone or together with another transcriptional activation tag, activates transcription in a cell of a gene to which the chimeric transcription activator protein binds;
(b) includes at least one ligand-binding domain which is heterologous with respect to at least two of the transcriptional activation tags of the composite transcription activation domain; and
(c) activates transcription of a gene to which the chimeric transcription activator protein binds in the presence of a ligand for the ligand binding domain.

4. A nucleic acid of claim 1 or 3 encoding a chimeric transcription activator protein comprising four or more transcriptional activation tags, wherein each transcriptional activation tag, alone or together with another transcriptional activation tag activates transcription of a gene to which the chimeric transcription activator protein binds.

5. A nucleic acid of claim 1 or 3 encoding a chimeric transcription activator protein having at least two transcriptional activation tags that synergize in activating transcription of a gene to which the chimeric transcription activator protein binds.

6. A nucleic acid of claim 1 or 3 encoding a chimeric transcription activator, wherein at least one transcriptional activation tags is selected from the group consisting of an alanine/proline-rich polypeptide, an acidic polypeptide, a proline-rich polypeptide, a serine/threonine rich polypeptide, and a glutamine-rich polypeptide.

7. A nucleic acid of claim 1 or 3 encoding a chimeric transcription activator, wherein at least one transcriptional activation tag is selected from the group consisting of the V8 domain of VP16 (SEQ ID NO: 3), the Vc domain of VP16, domain I of p65 (SEQ ID NO: 10), domain II of p65 (SEQ ID NO: 11) and the AP domain of p65 (amino acids 361–450).

8. A nucleic acid of claim 1 or 3 encoding a chimeric transcription activator, which activates transcription of a gene to which the transcription activator protein binds to a level that is at least 6-fold higher relative to activation of transcription of the same gene by VP16.

9. A nucleic acid of claim 1 or 3 encoding a chimeric transcription activator, which activates transcription of a gene to which the transcription activator protein binds to a level that is at least 8-fold higher relative to activation of transcription of the same by VP16.

10. A nucleic acid of claim 1 or 3 encoding a chimeric transcription activator, which activates transcription of a gene to which the transcription activator protein binds to a level that is at least 14–15-fold higher relative to activation of transcription of the same gene by VP16.

11. A nucleic acid of claim 1 or 3 encoding a chimeric transcription activator, which is not toxic to engineered cells expressing the transcriptional activator.

12. A nucleic acid of claim 3 which encodes a chimeric transcription activator protein, in which at least one of the ligand-binding domains binds to a cell permeant ligand.

13. A nucleic acid of claim 3 which encodes a chimeric transcription activator protein which further contains at least one DNA-binding domain.

14. A nucleic acid of claim 3, wherein the chimeric transcription activator induces expression of the gene in the presence of a ligand that binds the ligand-binding domain.

15. A nucleic acid of claim 4 encoding a chimeric transcription activator protein comprising five or more transcriptional activation tags, wherein each transcriptional activation tag, alone or together with another transcriptional activation tag, activates transcription of a gene to which the chimeric transcription activator protein binds.

16. A nucleic acid of claim 5, wherein at least two transcriptional activation tags synergize to induce an increase of a level of transcription by at least 2 fold relative to the level of transcription obtained with each of the transcriptional activation tags individually.

17. A nucleic acid composition comprising a first nucleic acid encoding a chimeric transcription activator protein of claim 12 and a second nucleic acid encoding a chimeric DNA-binding protein comprising at least one ligand binding domain for a cell permeant ligand and at least one DNA-binding domain.

18. A nucleic acid of claim 12, wherein the chimeric transcription activator protein further comprises at least one DNA-binding domain.

19. A nucleic acid of claim 3 or 13 encoding a chimeric transcription activator protein comprising at least two ligand-binding domain.

20. A nucleic acid of claim 3 or 13 encoding a chimeric transcription activator protein comprising at least three ligand-binding domains.

21. A nucleic acid of claim 15 encoding a chimeric transcription activator comprising ten or more transcriptional activation tags, wherein each transcriptional activation tag, alone or together with another transcriptional activation tag, activates transcription of a gene to which the chimeric transcription activator protein binds.

22. A nucleic acid composition of claim 17 in which the chimeric DNA-binding protein comprises two or more ligand-binding domains.

23. A nucleic acid composition of claim 17 which further comprises a target gene construct comprising a target gene operatively linked to an expression control sequence which includes a DNA sequence to which the chimeric DNA-binding protein binds.

24. A nucleic acid of claim 3, 12, 19 or 20 encoding a chimeric transcription activator protein, wherein at least one ligand binding domain is from FK506 binding protein (FKBP), cyclophilin, FRAP or a derivative thereof.

25. A nucleic acid of claim 3, 12, 19 or 20 wherein the ligand binding domain binds a macrolide.

26. A nucleic acid of claim 3, 12, 19 or 20, wherein the ligand binding domain binds a ligand selected from the group consisting of rapamycin, cyclosporin A, FK506, and FK1012.

27. A nucleic acid of claim 3, 12, 19 or 20 encoding a chimeric transcription activator protein, wherein the ligand binding domain is a steroid binding domain, an antibiotic binding domain, or a coumermycin binding domain.

28. A host cell comprising a nucleic acid composition of any of claims 2, 17, 22, or 23.

29. A method for producing a genetically engineered host cell, which method comprises introducing a nucleic acid composition of any of claims 2, 17, 22 or 23 into a host cell under conditions permitting uptake by the cell of nucleic acids, such that a genetically engineered host cell is produced.

30. A nucleic acid encoding a chimeric transcription activator protein which:
   (a) includes at least one composite transcription activation domain comprising two or more transcriptional activation tags which are mutually heterologous, wherein each transcriptional activation tag, alone or together with another transcriptional activation tag, activates transcription in a cell of a gene to which the chimeric transcription activator protein binds;
   (b) includes at least one ligand binding domain which is heterologous with respect to at least one of the transcriptional activation tags of the composite transcription activation domain, wherein the at least one ligand binding domain is derived from an immunophilin, a cyclophilin, a calcineurin, a FRAP or a DNA gyrase or from a receptor for tetracycline; and
   (c) activates transcription of a gene to which the chimeric transcription activator protein binds.

31. A method for stimulating expression of a target gene in a host cell, said host cell comprising:
   (i) a nucleic acid of claim 1, claim 13, or claim 30 encoding a chimeric transcription activator protein, and
   (ii) a target gene which is the target of the chimeric transcription activator protein, comprising maintaining the host cell under conditions suitable for gene expression stimulated by the chimeric transcription activator protein.

32. A method for stimulating expression of a target gene in a host cell, said host cell comprising:
   (i) a nucleic acid of claim 3, 12, or 30 encoding a chimeric transcription activator protein comprising at least one ligand-binding domain which binds a ligand,
   (ii) a second nucleic acid which encodes a chimeric protein comprising a DNA binding domain and a ligand binding domain which binds the ligand thereby forming a ligand cross-linked protein complex including the chimeric transcription activator protein, and
   (iii) a target gene which is the target of the ligand cross-linked protein complex,
comprising contacting the host cell with the ligand to stimulate expression of the target gene.

33. A nucleic acid encoding a chimeric transcription activator protein which:
   (a) includes at least one composite transcription activation domain comprising two or more transcriptional activation tags, at least two of which are mutually heterologous, wherein each transcriptional activation tag, alone or together with another transcriptional activation tag, activates transcription in a cell of a gene to which the chimeric transcription activator protein binds;
   (b) includes a bundling domain; and
   (c) activates transcription of a gene to which the chimeric transcription activator protein binds.

34. A host cell comprising a nucleic acid of any of claims 1, 3, 12, 13, 30 or 33.

35. A method for producing a genetically engineered host cell, which method comprises introducing a nucleic acid of any of claims 1, 3, 12, 13, 30 or 33 into a host cell under conditions permitting uptake by the cell of nucleic acids, such that a genetically engineered host cell is produced.

36. A nucleic acid of claim 33, further comprising at least one ligand binding domain.

37. A nucleic acid of claim 33, wherein the bundling domain is a dimerizing domain.

38. A nucleic acid of claim 33, wherein the bundling domain is a tetramerization domain.

39. A nucleic acid of claim 33, wherein the chimeric transcription activator protein further comprises at least one DNA-binding domain.

40. A nucleic acid of claim 3 or 33 encoding a chimeric transcription activator protein, wherein the composite transcription activation domain comprises at least two transcriptional activation tags, each of which, alone or together with another transcriptional activation tag, activates transcription of a gene to which the chimeric transcription activator protein binds.

41. A host cell of claim 34 further comprising a genomically-integrated target gene, to which the chimeric transcription activator protein binds.

42. A nucleic acid of claim 38, wherein the tetramerization domain is from *E. coli* lac repressor.

43. A host cell comprising
   (I) a nucleic acid encoding a chimeric transcription activator protein which:
      (a) includes a DNA-binding domain that binds to a target DNA sequence; and
      (b) includes a composite transcription activation domain comprising two transcriptional activation tags that are heterologous to one another, and to the DNA-binding domain,
   wherein the level of transcription of a gene including the target DNA sequence is dependent on the presence of each of the transcriptional activation tags; and
   (II) a genomically integrated target gene including the target DNA sequence.

44. A host cell comprising
   (I) a nucleic acid encoding a chimeric transcription activator protein which:
      (a) includes a ligand binding domain which binds a selected ligand; and
      (b) includes a composite transcription activation domain comprising two transcriptional activation tags that are heterologous to one another, and to the ligand-binding domain, and
   (II) a genomically integrated target gene which is transcribed in a manner dependent upon the presence of the chimeric transcription activator protein and the ligand,
wherein the level of transcription of the target gene is dependent on the presence of each of the transcriptional activation tags of the chimeric transcription activator protein.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
       (A) LENGTH: 2444 base pairs
       (B) TYPE: nucleic acid
       (C) STRANDEDNESS: both
       (D) TOPOLOGY: linear (ii) MOLECULE TYPE: cDNA (ix) FEATURE:
       (A) NAME/KEY: CDS
       (B) LOCATION: 39..1649

(xi) SEQUENCE DESCRIPTION: SEQ ID NO:1:

```
GGCACGAGGC GGGGCCGGGT CGCAGCTGGG CCCGCGGC ATG GAC GAA CTG TTC              53
                                          Met Asp Glu Leu Phe
                                            1               5

CCC CTC ATC TTC CCG GCA GAG CAG CCC AAG CAG CGG GGC ATG CGC TTC          101
Pro Leu Ile Phe Pro Ala Glu Gln Pro Lys Gln Arg Gly Met Arg Phe
             10                  15                  20

CGC TAC AAG TGC GAG GGG CGC TCC GCG GGC AGC ATC CCA GGC GAG AGG          149
Arg Tyr Lys Cys Glu Gly Arg Ser Ala Gly Ser Ile Pro Gly Glu Arg
         25                  30                  35

AGC ACA GAT ACC ACC AAG ACC CAC CCC ACC ATC AAG ATC AAT GGC TAC          197
Ser Thr Asp Thr Thr Lys Thr His Pro Thr Ile Lys Ile Asn Gly Tyr
     40                  45                  50

ACA GGA CCA GGG ACA GTG CGC ATC TCC CTG GTC ACC AAG GAC CCT CCT          245
Thr Gly Pro Gly Thr Val Arg Ile Ser Leu Val Thr Lys Asp Pro Pro
 55                  60                  65

CAC CGG CCT CAC CCC CAC GAG CTT GTA GGA AAG GAC TGC CGG GAT GGC          293
His Arg Pro His Pro His Glu Leu Val Gly Lys Asp Cys Arg Asp Gly
 70                  75                  80                  85

TTC TAT GAG GCT GAG CTC TGC CCG GAC CGC TGC ATC CAC AGT TTC CAG          341
Phe Tyr Glu Ala Glu Leu Cys Pro Asp Arg Cys Ile His Ser Phe Gln
                 90                  95                 100

AAC CTG GGA ATC CAG TGT GTG AAG AAG CGG GAC CTG GAG CAG GCT ATC          389
Asn Leu Gly Ile Gln Cys Val Lys Lys Arg Asp Leu Glu Gln Ala Ile
            105                 110                 115

AGT CAG CGC ATC CAG ACC AAC AAC AAC CCC TTC CAA GTT CCT ATA GAA          437
Ser Gln Arg Ile Gln Thr Asn Asn Asn Pro Phe Gln Val Pro Ile Glu
        120                 125                 130

GAG CAG CGT GGG GAC TAC GAC CTG AAT GCT GTG CGG CTC TGC TTC CAG          485
Glu Gln Arg Gly Asp Tyr Asp Leu Asn Ala Val Arg Leu Cys Phe Gln
    135                 140                 145

GTG ACA GTG CGG GAC CCA TCA GGC AGG CCC CTC CGC CTG CCG CCT GTC          533
```

```
                Val Thr Val Arg Asp Pro Ser Gly Arg Pro Leu Arg Leu Pro Pro Val
                150                 155                 160                 165

CTT TCT CAT CCC ATC TTT GAC AAT CGT GCC CCC AAC ACT GCC GAG CTC                581
Leu Ser His Pro Ile Phe Asp Asn Arg Ala Pro Asn Thr Ala Glu Leu
            170                 175                 180

AAG ATC TGC CGA GTG AAC CGA AAC TCT GGC AGC TGC CTC GGT GGG GAT                629
Lys Ile Cys Arg Val Asn Arg Asn Ser Gly Ser Cys Leu Gly Gly Asp
                185                 190                 195

GAG ATC TTC CTA CTG TGT GAC AAG GTG CAG AAA GAG GAC ATT GAG GTG                677
Glu Ile Phe Leu Leu Cys Asp Lys Val Gln Lys Glu Asp Ile Glu Val
            200                 205                 210

TAT TTC ACG GGA CCA GGC TGG GAG GCC CGA GGC TCC TTT TCG CAA GCT                725
Tyr Phe Thr Gly Pro Gly Trp Glu Ala Arg Gly Ser Phe Ser Gln Ala
        215                 220                 225

GAT GTG CAC CGA CAA GTG GCC ATT GTG TTC CGG ACC CCT CCC TAC GCA                773
Asp Val His Arg Gln Val Ala Ile Val Phe Arg Thr Pro Pro Tyr Ala
230                 235                 240                 245

GAC CCC AGC CTG CAG GCT CCT GTG CGT GTC TCC ATG CAG CTG CGG CGG                821
Asp Pro Ser Leu Gln Ala Pro Val Arg Val Ser Met Gln Leu Arg Arg
                250                 255                 260

CCT TCC GAC CGG GAG CTC AGT GAG CCC ATG GAA TTC CAG TAC CTG CCA                869
Pro Ser Asp Arg Glu Leu Ser Glu Pro Met Glu Phe Gln Tyr Leu Pro
            265                 270                 275

GAT ACA GAC GAT CGT CAC CGG ATT GAG GAG AAA CGT AAA AGG ACA TAT                917
Asp Thr Asp Asp Arg His Arg Ile Glu Glu Lys Arg Lys Arg Thr Tyr
        280                 285                 290

GAG ACC TTC AAG AGC ATC ATG AAG AAG AGT CCT TTC AGC GGA CCC ACC                965
Glu Thr Phe Lys Ser Ile Met Lys Lys Ser Pro Phe Ser Gly Pro Thr
    295                 300                 305

GAC CCC CGG CCT CCA CCT CGA CGC ATT GCT GTG CCT TCC CGC AGC TCA               1013
Asp Pro Arg Pro Pro Pro Arg Arg Ile Ala Val Pro Ser Arg Ser Ser
310                 315                 320                 325

GCT TCT GTC CCC AAG CCA GCA CCC CAG CCC TAT CCC TTT ACG TCA TCC               1061
Ala Ser Val Pro Lys Pro Ala Pro Gln Pro Tyr Pro Phe Thr Ser Ser
                330                 335                 340

CTG AGC ACC ATC AAC TAT GAT GAG TTT CCC ACC ATG GTG TTT CCT TCT               1109
Leu Ser Thr Ile Asn Tyr Asp Glu Phe Pro Thr Met Val Phe Pro Ser
            345                 350                 355

GGG CAG ATC AGC CAG GCC TCG GCC TTG GCC CCG GCC CCT CCC CAA GTC               1157
Gly Gln Ile Ser Gln Ala Ser Ala Leu Ala Pro Ala Pro Pro Gln Val
        360                 365                 370

CTG CCC CAG GCT CCA GCC CCT GCC CCT GCT CCA GCC ATG GTA TCA GCT               1205
Leu Pro Gln Ala Pro Ala Pro Ala Pro Ala Pro Ala Met Val Ser Ala
375                 380                 385

CTG GCC CAG GCC CCA GCC CCT GTC CCA GTC CTA GCC CCA GGC CCT CCT               1253
Leu Ala Gln Ala Pro Ala Pro Val Pro Val Leu Ala Pro Gly Pro Pro
390                 395                 400                 405

CAG GCT GTG GCC CCA CCT GCC CCC AAG CCC ACC CAG GCT GGG GAA GGA               1301
Gln Ala Val Ala Pro Pro Ala Pro Lys Pro Thr Gln Ala Gly Glu Gly
                410                 415                 420

ACG CTG TCA GAG GCC CTG CTG CAG CTG CAG TTT GAT GAT GAA GAC CTG               1349
Thr Leu Ser Glu Ala Leu Leu Gln Leu Gln Phe Asp Asp Glu Asp Leu
            425                 430                 435

GGG GCC TTG CTT GGC AAC AGC ACA GAC CCA GCT GTG TTC ACA GAC CTG               1397
Gly Ala Leu Leu Gly Asn Ser Thr Asp Pro Ala Val Phe Thr Asp Leu
        440                 445                 450

GCA TCC GTC GAC AAC TCC GAG TTT CAG CAG CTG CTG AAC CAG GGC ATA               1445
Ala Ser Val Asp Asn Ser Glu Phe Gln Gln Leu Leu Asn Gln Gly Ile
    455                 460                 465

CCT GTG GCC CCC CAC ACA ACT GAG CCC ATG CTG ATG GAG TAC CCT GAG               1493
```

```
                Pro Val Ala Pro His Thr Thr Glu Pro Met Leu Met Glu Tyr Pro Glu
                470                 475                 480                 485

GCT ATA ACT CGC CTA GTG ACA GCC CAG AGG CCC CCC GAC CCA GCT CCT              1541
Ala Ile Thr Arg Leu Val Thr Ala Gln Arg Pro Pro Asp Pro Ala Pro
                490                 495                 500

GCT CCA CTG GGG GCC CCG GGG CTC CCC AAT GGC CTC CTT TCA GGA GAT              1589
Ala Pro Leu Gly Ala Pro Gly Leu Pro Asn Gly Leu Leu Ser Gly Asp
            505                 510                 515

GAA GAC TTC TCC TCC ATT GCG GAC ATG GAC TTC TCA GCC CTG CTG AGT              1637
Glu Asp Phe Ser Ser Ile Ala Asp Met Asp Phe Ser Ala Leu Leu Ser
            520                 525                 530

CAG ATC AGC TCC TAAGGGGTG ACGCCTGCCC TCCCCAGAGC ACTGGTTGCA                   1689
Gln Ile Ser Ser
        535

GGGGATTGAA GCCCTCCAAA AGCACTTACG GATTCTGGTG GGGTGTGTTC CAACTGCCCC            1749

CAACTTTGTG GATGTCTTCC TTGGAGGGGG GAGCCATATT TTATTCTTTT ATTGTCAGTA            1809

TCTGTATCTC TCTCTCTTTT TGGAGGTGCT TAAGCAGAAG CATTAACTTC TCTGGAAAGG            1869

GGGGAGCTGG GGAAACTCAA ACTTTTCCCC TGTCCTGATG GTCAGCTCCC TTCTCTGTAG            1929

GGAACTGTGG GGTCCCCCAT CCCCATCCTC CAGCTTCTGG TACTCTCCTA GAGACAGAAG            1989

CAGGCTGGAG GTAAGGCCTT TGAGCCCACA AAGCCTTATC AAGTGTCTTC CATCATGGAT            2049

TCATTACAGC TTAATCAAAA TAACGCCCCA GATACCAGCC CCTGTATGGC ACTGGCATTG            2109

TCCCTGTGCC TAACACCAGC GTTTGAGGGG CTGCCTTCCT GCCCTACAGA GGTCTCTGCC            2169

GGCTCTTTCC TTGCTCAACC ATGGCTGAAG GAAACAGTGC AACAGCACTG GCTCTCTCCA            2229

GGATCCAGAA GGGGTTTGGT CTGGACTTCC TTGCTCTCCC CTCTTCTCAA GTGCCTTAAT            2289

AGTAGGGTAA GTTGTTAAGA GTGGGGGAGA GCAGGCTGGG AGCTCTCCAG TCAGGAGGCA            2349

TAGTTTTTAG TGAACAATCA AAGCACTTGG ACTCTTGCTC TTTCTACTCT GAACTAATAA            2409

AGCTGTTGCC AAGCTGGACG GCACGAGCTC GTGCC                                       2444

(2) INFORMATION FOR SEQ ID NO:2:

(i) SEQUENCE CHARACTERISTICS:
        (A) LENGTH: 537 amino acids
        (B) TYPE: amino acid
        (D) TOPOLOGY: linear (ii) MOLECULE TYPE: protein (xi) SEQUENCE DESCRIPTION: SEQ ID NO:2:

Met Asp Glu Leu Phe Pro Leu Ile Phe Pro Ala Glu Gln Pro Lys Gln
1               5                   10                  15

Arg Gly Met Arg Phe Arg Tyr Lys Cys Glu Gly Arg Ser Ala Gly Ser
            20                  25                  30

Ile Pro Gly Glu Arg Ser Thr Asp Thr Thr Lys Thr His Pro Thr Ile
        35                  40                  45

Lys Ile Asn Gly Tyr Thr Gly Pro Gly Thr Val Arg Ile Ser Leu Val
    50                  55                  60

Thr Lys Asp Pro Pro His Arg Pro His Pro His Glu Leu Val Gly Lys
65                  70                  75                  80

Asp Cys Arg Asp Gly Phe Tyr Glu Ala Glu Leu Cys Pro Asp Arg Cys
                85                  90                  95

Ile His Ser Phe Gln Asn Leu Gly Ile Gln Cys Val Lys Lys Arg Asp
            100                 105                 110

Leu Glu Gln Ala Ile Ser Gln Arg Ile Gln Thr Asn Asn Asn Pro Phe
        115                 120                 125
```

```
Gln Val Pro Ile Glu Glu Gln Arg Gly Asp Tyr Asp Leu Asn Ala Val
    130                 135                 140
Arg Leu Cys Phe Gln Val Thr Val Arg Asp Pro Ser Gly Arg Pro Leu
145                 150                 155                 160
Arg Leu Pro Pro Val Leu Ser His Pro Ile Phe Asp Asn Arg Ala Pro
                165                 170                 175
Asn Thr Ala Glu Leu Lys Ile Cys Arg Val Asn Arg Asn Ser Gly Ser
            180                 185                 190
Cys Leu Gly Gly Asp Glu Ile Phe Leu Leu Cys Asp Lys Val Gln Lys
        195                 200                 205
Glu Asp Ile Glu Val Tyr Phe Thr Gly Pro Gly Trp Glu Ala Arg Gly
    210                 215                 220
Ser Phe Ser Gln Ala Asp Val His Arg Gln Val Ala Ile Val Phe Arg
225                 230                 235                 240
Thr Pro Pro Tyr Ala Asp Pro Ser Leu Gln Ala Pro Val Arg Val Ser
                245                 250                 255
Met Gln Leu Arg Arg Pro Ser Asp Arg Glu Leu Ser Glu Pro Met Glu
            260                 265                 270
Phe Gln Tyr Leu Pro Asp Thr Asp Asp Arg His Arg Ile Glu Glu Lys
        275                 280                 285
Arg Lys Arg Thr Tyr Glu Thr Phe Lys Ser Ile Met Lys Lys Ser Pro
    290                 295                 300
Phe Ser Gly Pro Thr Asp Pro Arg Pro Pro Arg Arg Ile Ala Val
305                 310                 315                 320
Pro Ser Arg Ser Ser Ala Ser Val Pro Lys Pro Ala Pro Gln Pro Tyr
                325                 330                 335
Pro Phe Thr Ser Ser Leu Ser Thr Ile Asn Tyr Asp Glu Phe Pro Thr
            340                 345                 350
Met Val Phe Pro Ser Gly Gln Ile Ser Gln Ala Ser Ala Leu Ala Pro
        355                 360                 365
Ala Pro Pro Gln Val Leu Pro Gln Ala Pro Ala Pro Ala Pro Ala Pro
    370                 375                 380
Ala Met Val Ser Ala Leu Ala Gln Ala Pro Ala Pro Val Pro Val Leu
385                 390                 395                 400
Ala Pro Gly Pro Pro Gln Ala Val Ala Pro Pro Ala Pro Lys Pro Thr
                405                 410                 415
Gln Ala Gly Glu Gly Thr Leu Ser Glu Ala Leu Leu Gln Leu Gln Phe
            420                 425                 430
Asp Asp Glu Asp Leu Gly Ala Leu Leu Gly Asn Ser Thr Asp Pro Ala
        435                 440                 445
Val Phe Thr Asp Leu Ala Ser Val Asp Asn Ser Glu Phe Gln Gln Leu
    450                 455                 460
Leu Asn Gln Gly Ile Pro Val Ala Pro His Thr Thr Glu Pro Met Leu
465                 470                 475                 480
Met Glu Tyr Pro Glu Ala Ile Thr Arg Leu Val Thr Ala Gln Arg Pro
                485                 490                 495
Pro Asp Pro Ala Pro Ala Pro Leu Gly Ala Pro Gly Leu Pro Asn Gly
            500                 505                 510
Leu Leu Ser Gly Asp Glu Asp Phe Ser Ser Ile Ala Asp Met Asp Phe
        515                 520                 525
Ser Ala Leu Leu Ser Gln Ile Ser Ser
    530                 535
```

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

```
Asp Phe Asp Leu Asp Met Leu Gly
1               5
```

(2) INFORMATION FOR SEQ ID NO:4:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

```
Asn Phe Leu Gln Leu Pro Gln Gln Thr Gln Gly Ala Leu Leu Thr Ser
1               5                   10                  15
Gln Pro
```

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Ser Tyr Gly Gln Gln Ser
1               5
```

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Arg Gly Gly Asn Pro Glu
1               5
```

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

```
Gly Gly Asn Gln Ala
1               5
```

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

```
Pro Lys Lys Lys Arg Lys Val
1               5
```

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

```
Gly Gly Gly Gly Ser Gly Gly Gly Ser Gly Gly Gly Gly Ser
1               5                   10                  15
```

(2) INFORMATION FOR SEQ ID NO:10:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

```
Ser Ala Leu Ala Leu Ala Pro Ala Pro Pro Gln Val Leu Pro Gln Ala
1               5                   10                  15
Pro Ala Pro Ala Pro Ala Pro Ala Met Val
            20                  25
```

(2) INFORMATION FOR SEQ ID NO:11:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

```
Ser Ala Leu Ala Gln Ala Pro Ala Pro Val Pro Val Leu Ala Pro Gly
1               5                   10                  15
Pro Pro Gln Ala Val Ala Pro Pro Ala Pro
            20                  25
```